United States Patent
Patolsky et al.

(10) Patent No.: US 10,422,780 B2
(45) Date of Patent: Sep. 24, 2019

(54) ELECTROCHEMICAL DETECTION OF PEROXIDE-CONTAINING COMPOUNDS

(71) Applicant: Ramot at Tel-Aviv University Ltd., Tel-Aviv (IL)

(72) Inventors: Fernando Patolsky, Rehovot (IL); Vadim Krivitsky, Bney-Ayish (IL); Boris Filanovsky, Bat-Yam (IL)

(73) Assignee: Ramot at Tel-Aviv University Ltd., Tel-Aviv (IL)

( * ) Notice: Subject to any disclaimer, the term of this patent is extended or adjusted under 35 U.S.C. 154(b) by 0 days.

(21) Appl. No.: 16/008,215

(22) Filed: Jun. 14, 2018

(65) Prior Publication Data
US 2018/0364209 A1 Dec. 20, 2018

Related U.S. Application Data
(60) Provisional application No. 62/519,977, filed on Jun. 15, 2017.

(51) Int. Cl.
*G01N 27/28* (2006.01)
*G01N 27/30* (2006.01)
*G01N 33/00* (2006.01)

(52) U.S. Cl.
CPC ....... *G01N 33/0047* (2013.01); *G01N 27/286* (2013.01); *G01N 27/304* (2013.01); *G01N 27/308* (2013.01)

(58) Field of Classification Search
CPC ......... G01N 27/28; G01N 27/30; G01N 33/00
USPC ...... 422/82.01–82.03, 98; 436/135, 149–151
See application file for complete search history.

(56) References Cited

U.S. PATENT DOCUMENTS

| | | | |
|---|---|---|---|
| 3,389,963 A | | 6/1968 | Baumgartner et al. |
| 4,299,682 A | * | 11/1981 | Oda .......................... C25B 1/46 204/265 |
| 4,647,359 A | * | 3/1987 | Lindstrom ............ C25B 11/035 156/280 |
| 4,795,542 A | * | 1/1989 | Ross .................. G01N 27/3271 204/403.09 |
| 5,480,808 A | * | 1/1996 | Kauffman .............. G01N 27/48 422/82.02 |
| 5,795,453 A | * | 8/1998 | Gilmartin ............ G01N 31/228 204/403.03 |
| 5,897,758 A | * | 4/1999 | Musacchio ........ G01N 27/3335 204/416 |

(Continued)

FOREIGN PATENT DOCUMENTS

| CN | 103323516 | 9/2013 |
|---|---|---|
| CN | 103852512 | 6/2014 |

(Continued)

OTHER PUBLICATIONS

Garjonyte, R. et al, Sensors and Actuators B 1998, 46, 236-241.*

(Continued)

*Primary Examiner* — Arlen Soderquist

(57) ABSTRACT

A sensing electrode, and an electrochemical system and method utilizing same for detecting peroxide-containing compounds in a sample, are provided. The sensing electrode is a carbon electrode having ions of a metal that promotes decomposition of a peroxide absorbed to its surface, optionally along with a solid electrolyte membrane.

Figures 3A, 3B, 3C:
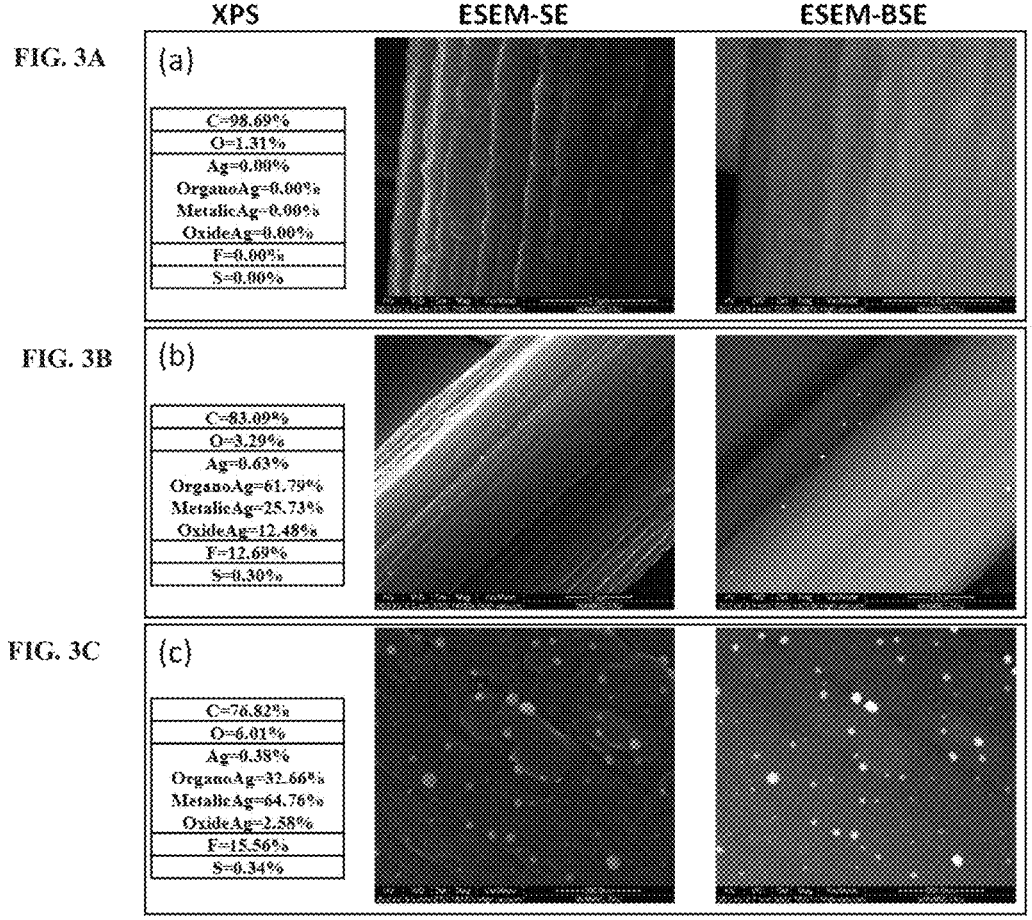

23 Claims, 5 Drawing Sheets
(3 of 5 Drawing Sheet(s) Filed in Color)

(56) References Cited

U.S. PATENT DOCUMENTS

| | | | |
|---|---|---|---|
| 6,129,831 A * | 10/2000 | Temmerman | G01N 27/308 204/294 |
| 6,309,535 B1 * | 10/2001 | Williams | G01N 27/308 204/294 |
| 6,872,786 B2 | 3/2005 | Murray et al. | |
| 7,244,345 B1 | 7/2007 | Filanovsky | |
| 8,178,357 B2 * | 5/2012 | Trogler | G01N 33/0036 422/82.01 |
| 8,968,825 B1 * | 3/2015 | Kawde | B82Y 30/00 427/113 |
| 2003/0168338 A1 | 9/2003 | Gao et al. | |
| 2005/0051440 A1 * | 3/2005 | Simpson | A61B 5/14532 205/778 |
| 2006/0193750 A1 | 8/2006 | Filanovsky et al. | |
| 2006/0231420 A1 | 10/2006 | Garzon et al. | |
| 2009/0142649 A1 | 6/2009 | Fernandez Lopez et al. | |
| 2009/0275143 A1 * | 11/2009 | Misra | G01N 27/127 436/130 |
| 2010/0000882 A1 * | 1/2010 | Wang | G01N 33/0057 205/781 |
| 2010/0040863 A1 * | 2/2010 | Li | B22F 1/0018 428/323 |
| 2010/0112546 A1 | 5/2010 | Lieber et al. | |
| 2010/0187108 A1 * | 7/2010 | Matsumoto | G01N 27/4166 204/403.14 |
| 2010/0227382 A1 | 9/2010 | Lieber et al. | |
| 2010/0297776 A1 * | 11/2010 | Trogler | G01N 33/0036 436/135 |
| 2011/0033869 A1 * | 2/2011 | Bertin | G01N 33/5438 435/7.1 |
| 2011/0140885 A1 * | 6/2011 | Hummer | G08B 21/12 340/539.13 |
| 2011/0162977 A1 | 7/2011 | Lafitte et al. | |
| 2011/0180764 A1 * | 7/2011 | Takahashi | B22F 1/0018 252/514 |
| 2011/0306699 A1 * | 12/2011 | Whang | A01N 59/16 523/113 |
| 2012/0037513 A1 * | 2/2012 | Lindemann | C12Q 1/001 205/777.5 |
| 2013/0144131 A1 * | 6/2013 | Wang | A61B 5/1477 600/301 |
| 2014/0275597 A1 | 9/2014 | Zhang et al. | |
| 2016/0061775 A1 * | 3/2016 | Zabetakis | G01N 21/35 205/790.5 |
| 2017/0226647 A1 * | 8/2017 | Benetton | C25B 1/30 |
| 2017/0243911 A1 | 8/2017 | Patolsky et al. | |
| 2018/0045678 A1 * | 2/2018 | Dressick | G01N 27/30 |
| 2018/0372673 A1 | 12/2018 | Patolsky et al. | |

FOREIGN PATENT DOCUMENTS

| | | |
|---|---|---|
| CN | 103983680 | 8/2014 |
| WO | WO 2005/050157 | 6/2005 |
| WO | WO 2006/090401 | 8/2006 |
| WO | WO 2007/029245 | 3/2007 |
| WO | WO 2011/000443 | 1/2011 |
| WO | WO 2011/154939 | 12/2011 |
| WO | WO 2012/049616 | 4/2012 |
| WO | WO 2014/111944 | 7/2014 |
| WO | WO 2015/059704 | 4/2015 |
| WO | WO 2017/030930 | 2/2017 |
| WO | WO 2017/098518 | 6/2017 |
| WO | WO 2018/229780 | 12/2018 |

OTHER PUBLICATIONS

Kasanuki, T. et al, Chemical Sensors 2001, 17, Supplement B 427-429.*
Chen, S. et al, Carbon 2003, 41, 1265-1271.*
Schulte-Ladbeck, R. ert al, Chromatographia 2003, 57, Supplement, S61-S66.*
Langley, C. E. et al, Analytical Sciences 2007, 23, 165-170.*
Jin, G.-P. et al, Electroanalysis 2008, 20, 907-915.*
Lu, J. et al, ACS Nano 2008, 9, 1825-1832.*
Benedet, J. et al, Analytical and Bioanalytical Chemistry 2009, 395, 371-376.*
Campbell, F. W. et al, Journal of Physican CHemistry C 2009, 113, 9053-9062.*
Salimi, S. et al, Electrochimica Acta 2011, 56, 3387-3394.*
Liu, S. et al, Carbon 2011, 49, 3158-3164.*
Habibi, B. et al, Microchimica Acta 2012, 177, 185-193.*
Afraz, A. et al, Journal of Solid State Electrochemistry 2013, 17, 2017-2025.*
Goodman, P., PhD Thesis 2013, 208 pages.*
Li, X. et al, Electrochimica Acta 2013, 113, 170-175.*
Jia, X. et al, ACS Applied Materials & Interfaces 2013, 5, 12017-12022.*
Dong, S. et al, Analytical Chemistry 2013, 85, 11739-11746.*
Lorestani, F. et al, Sensors and Actuators B 2015, 208, 389-398.*
Mani, V. et al, Electrochimica Acta 2015, 176, 804-810.*
Li, Y. et al, Nanomaterials 2015, 5, 1891-1905.*
Mbah, J. C. et al, Sensors and Actuators B 2016, 222, 693-697.*
Bratin et al. "Determination of Nitro Aromatic, Nitramine, and Nitrate Ester Explosive Compounds in Explosive Mixtures and Gunshot Residue by Liquid Chromatography and Reductive Electrochemical Detection", Analytica Chimica Acta, 130(2): 295-311, Oct. 1981.
Buckshire "An Overview of Carbon Fiber Electrodes Used in Neurochemical Monitoring", Thesis Submitted to the Graduate Faculty of Arts and Sciences in Partial Fulfillment of the Requirements for the Degree of Master of Science, Chemistry, University of Pittsburgh, USA, p. 1-34, Jun. 13, 2008.
Butler et al. "Removal of Dissolved Oxygen From Water: A Comparison of Four Common Techniques", Talanta, 41(2): 211-215, Feb. 1994.
Chaki et al. "Single Phase Preparation of Monodispersed Silver Nanoclusters Using a Unique Electron Transfer and Cluster Stabilising Agent, Triethylamine", Chemical Communications, 2002(1): 76-77, Advance Publication Dec. 11, 2001.
Chaubey et al. "Mediated Biosensors", Biosensors & Bioelectronics, 17(6-7): 441-456, Jun. 26, 2002.
Chen et al. "Determination of Explosives Using Electrochemically Reduced Graphene", Chemistry—An Asian Journal, 6(5): 1210-1216, Published Online Mar. 8, 2011.
Chen et al. "Poly[Meso-Tetrakis(2-Thienyl)Pophyrin] for the Sensitive Electrochemical Detection of Explosives", Sensors and Actuators B: Chemical, 147(1): 191-197, Available Online Mar. 17, 2010.
Cizek et al. "Integrated Explosive Preconcentrator and Electrochemical Detection System for 2,4,6-Trinitrotoluene (TNT) Vapor", Analytica Chimica Acta, 661(1): 117-121, Available Online Dec. 16, 2009.
Dubnikova et al. "Novel Approach to the Detection of Triacetone Triperoxide (TATP): Its Structure and Its Complexes With Ions", The Journal of Physical Chemistry A, 106(19): 4951-4956, Apr. 18, 2002.
Dwivedy et al. "Charge-Transfer Complexes of 2,4,6-Trinitrotoluene and M-Dinitrobenzene With Some Amines", Journal of Chromatography A, 29(1): 120-125, Jul. 1967.
Engel et al. "Supersensitive Detection of Explosives by Silicon Nanowire Arrays", Angewandte Chemie, International Edition, 49(38): 6830-6835, Sep. 10, 2010.
Eren et al. "Determination of Peroxide-Based Explosives With Copper(II)-Nepcuproine Assay Combined With a Molecular Spectroscopic Sensor", The Analyst, 135(8): 2085-2091, Published Online Jun. 7, 2010.
Filanovsky et al. "Carbon Electrodes Modified With TiO2/Metal Nanoparticles and Their Application to the Detection of Trinitrotoluene", Advanced Functional Materials, 17(9): 1487-1492, Published Online Apr. 18, 2007.
Galik et al. "Cyclic and Square-Wave Voltammetric Signatures of Nitro-Containing Explosives", Electroanalysis, 23(5): 1193-1204, May 2011.
Grigoriants et al. "Electrochemical Reduction of Trinitrotoluene on Core-Shell Tin-Carbon Electrodes", Electrochimica Acta, 54(2): 690-697, Available Online Jul. 11, 2008.

(56) References Cited

OTHER PUBLICATIONS

Guo et al. "Porphyrin Functionalized Graphene for Sensitive Electrochemical Detection of Ultratrace Explosives", Electroanalysis, 23(4): 885-893, Apr. 2011.
Laine et al. "Analysis of Hydrogen Peroxide and an Organic Hydroperoxide Via the Electrocatalytic Fenton Reaction", Microchemical Journal, 91(1): 78-81, Available Online Aug. 22, 2008.
Laine et al. "Electrochemical Detection of Triacetone Triperoxide Employing the Electrocatalytic Reaction of Iron(II/III)-Ethylenediaminetetraacetate and Hydrogen Peroxide", Analytica Chimica Acta, 608: 56-60, Published Online Dec. 8, 2007.
Lichtenstein et al. "Supersensitive Fingerprinting of Explosives by Chemically Modified Nanosensors Arrays", Nature Communications, 5: 4195-1-4195-12, Jun. 24, 2014.
Lu et al. "Highly Sensitive Electrochemical Detection of Trace Liquid Peroxide Explosives at a Prussian-Blue 'Artificial-Peroxide' Modified Electrode", The Analyst, 131(12): 1279-1281, Published in Advance Oct. 12, 2006.
Marinovic et al. "The Electrochemical Reduction of Trinitrotoluene on a Platinum Wire Modified by Chemisorbed Acetonitrile", Journal of Electroanalytical Chemistry, 648(1): 1-7, Available Online Jul. 15, 2010.
Munoz et al. "'One-Step' Simplified Electrochemical Sensing of TATP Based on Its Acid Treatment", The Analyst, 132(6): 560-565, Published in Advance Apr. 30, 2007.
Parajuli et al. "Sensitive Determination of Hexamethylene Triperoxide Diamine Explosives, Using Electrogenerated Chemiluminescence Enhanced by Silver Nitrate", Analytical Chemistry, 81(13): 5267-5272, Published on Web Jun. 10, 2009.
Schulte-Ladbeck et al. "A Field Test for the Detection of Peroxide-Based Explosives", The Analyst, 127(9): 1152-1154, Published in Advance Aug. 16, 2002.
Schulte-Ladbeck et al. "Determination of Triacetonetriperoxide in Ambient Air", Analytica Chimica Acta, 482(2): 183-188, Apr. 15, 2003.
Schulte-Ladbeck et al. "Trace Analysis of Peroxide-Based Explosives", Analytical Chemistry, 75(4): 731-735, Published on Web Jan. 15, 2003.
Sheppard et al. "Electrochemical and Microscopic Characterisation of Platinum-Coated Perfluorosulfonic Acid (Nafion 117) Materials", Analyst, 123(10): 1923-1929, 1998.
Spalek et al. "Kinetics of the Decomposition of Hydrogen Peroxide in Alkaline Solutions", Journal of the Chemical Society, Faraday Transactions I: Physical Chemistry in Condensed Phases, 78(8): 2349-2359, 1982.
Wang et al. "A Single-Walled Carbon Nanotube Network Gas Sensing Device", Sensors, 11(8): 7763-7772, Aug. 8, 2011.
Weiss "The Catalytic Decomposition of Hydrogen Peroxide on Different Metals", Transactions of the Faraday Society, 31: 1547-1557, 1935.
Zang et al. "Electrochemical Detection of Ultratrace Nitroaromatic Explosives Using Ordered Mesoporous Carbon", Analytica Chimica Acta, 683(2): 187-191, Available Online Oct. 20, 2010.
Zhao et al. "Electrocatalytic Reduction of Hydrogen Peroxide by Iron-Adenosine Nucleotide Complexes", Journal of Electroanalytical Chemistry, 379(1-2): 501-503, Dec. 12, 1994.
Xie et al. "Selective and Rapid Detection of Triacetone Triperoxide by Double-Step Chronoamperometry", Microchemical Journal, 94(2): 166-170, Available Online Oct. 31, 2009.
International Search Report and the Written Opinion dated Oct. 10, 2018 From the International Searching Authority Re. Application No. PCT/IL2018/050665. (12 Pages).
Official Action dated Aug. 24, 2018 From the U.S. Patent and Trademark Office Re. U.S. Appl. No. 16/008,218. (16 pages).
Lu et al. "Determination of Explosives Based on Novel Type of Sensor Using Porphyrin Functionalized Carbon Nanotubes", Colloids and Surfaces B: Biointerfaces, 88: 396-401, Available Online Jul. 18, 2011.
Sablok et al. "Amine Functionalized Graphene Oxide/CNT Nanocomposite for Ultrasensitive Electrochemical Detection of Trinitroluene", Journal of Hazardous Materials, 248-249: 322-328, Published Online Jan. 23, 2013.
Shamsipur et al. "A High Sensitive TNT Sensor Based on Electrochemically Reduced Graphene Oxide-Poly(Amidoamine) Modified Electrode", Electroanalysis, 27(6): 1466-1472, Published Online Mar. 18, 2015.
International Search Report and the Written Opinion dated Oct. 11, 2018 From the International Searching Authority Re. Application No. PCT/IL2018/050666. (13 Pages).
Kumaravel et al. "A Novel Nanosilver/Nafion Composite Electrode for Electrochemical Sensing of Methyl Parathion and Parathion", Journal of Electroanalytical Chemistry, 638(2): 231-235, Available Online Nov. 6, 2009.
Mamo et al. "Development of a Molecularly Imprinted Polymer-Based Sensor for the Electrochemical Determination of Triacetone Triperoxide (TATP)", Sensors, 14(12): 23269-23282, Published Online Dec. 5, 2014.
Welch et al. "Silver Nanoparticle Assemblies Supported on Glassy-Carbon Electrodes for the Electro-Analytical Detection of Hydrogen Peroxide", Analytical and Bioanalytical Chemistry, 382(1): 12-21, Published Online Apr. 26, 2005.
Official Action dated Feb. 26, 2019 From the U.S. Patent and Trademark Office Re. U.S. Appl. No. 16/008,218. (19 pages).
Requisition by the Examiner dated Feb. 8, 2019 From the Innovation, Science and Economic Development Canada, Canadian Intellectual Property Office Re. Application No. 3,020,655. (7 pages).
Requisition by the Examiner dated Feb. 15, 2019 From the Innovation, Science and Economic Development Canada, Canadian Intellectual Property Office Re. Application No. 3,020,573. (6 Pages).
Fu et al. "Amino Functionalized Mesoporous Silica Microspheres With Perpendicularly Aligned Mesopore Channels for Electrochemical Detection of Trace 1,4,6-Trinitrotoluene", Electrochimica Acta, 56(1): 102-107, Available Online Sep. 21, 2010.
Halouzka et al. "Nanostructured Silver and Platinum Modified Carbon Fiber Microelectrodes Coated With Nafion for H2O2 Determination", Journal of Biochemcial Technology, 2(5): S70-S73, Publisched Online Oct. 25, 2011.
Halouzka et al. "Silver-Nafion Coated Cylindrical Carbon Fiber Microelectrode for Amperometric Monitoring of Hydrogen Peroxide Heterogeneous Catalytic Decomposition", Chemical Engineering Journal, 165(3): 813-818, Dec. 15, 2010.
Marwan et al. "Functionalization of Glassy Carbon Electrodes With Metal-Based Species", Chemical Materials, 17(9): 2395-2403, Published on Web Apr. 8, 2005.
Nia et al. "Hydrogen Peroxide Sensor: Uniformly Decorated Silver Nanoparticles on Polypyrrole for Wide Detection Range", Applied Surface Science, 357(Part B): 1565-1572, Dec. 1, 2015.
Ojani et al. "Electrocatalytic Oxidation of Hydrogen Peroxide on Poly(M-Toluidine)-Nickel Modified Carbon Paste Electrode in Alkaline Medium", Electroanalysis, 22(14): 1607-1616, Jul. 2010.
Parajuli "Sensitive Detection of High Explosives Using Electrogenerated Chemiluminescence", Abstract of a Dissertation Submitted to the Graduate School of the University of Southern Mississippi in Partial Fulfillment of the Requirements for the Degree of Doctor of Philisophy, p. 1-126, May 2011.
Vu et al. "Electrochemical Detection of TNT by Differential Pulse Adsorptive Stripping Voltammetry at Carbon Paste Electrode Modified by 1-Butyl-3-Methylimidazolium Tetrafluoroborate", Bulletin of the Korean Chemical Society, 37(3): 378-385, Published Online Feb. 22, 2016.

\* cited by examiner

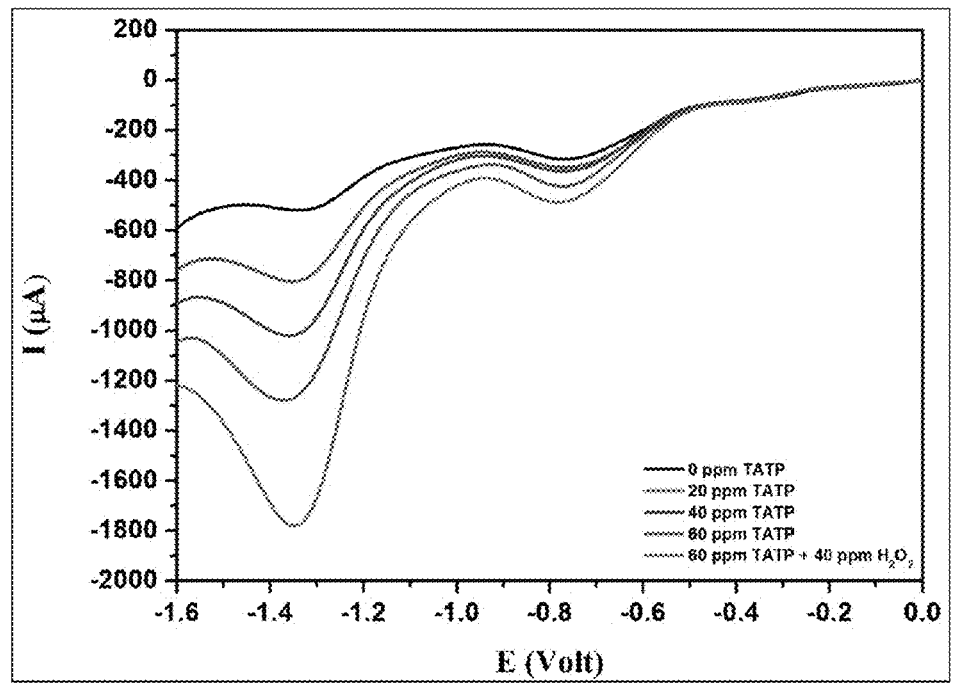
FIG. 1
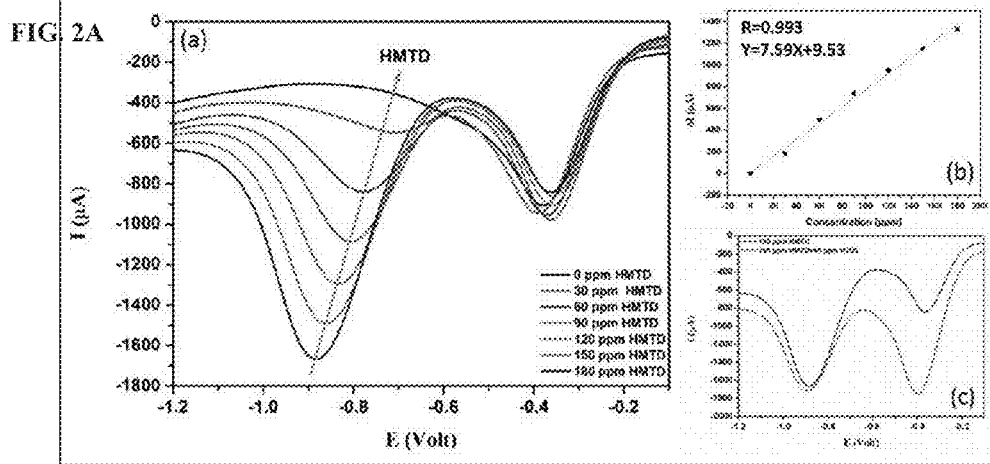
FIG. 2A
FIG. 2B
FIG. 2C

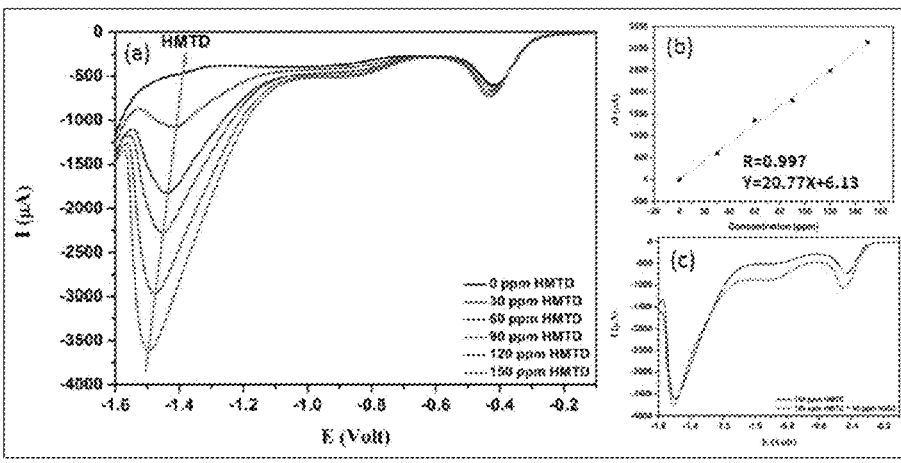
FIG. 4A
FIG. 4B
FIG. 4C
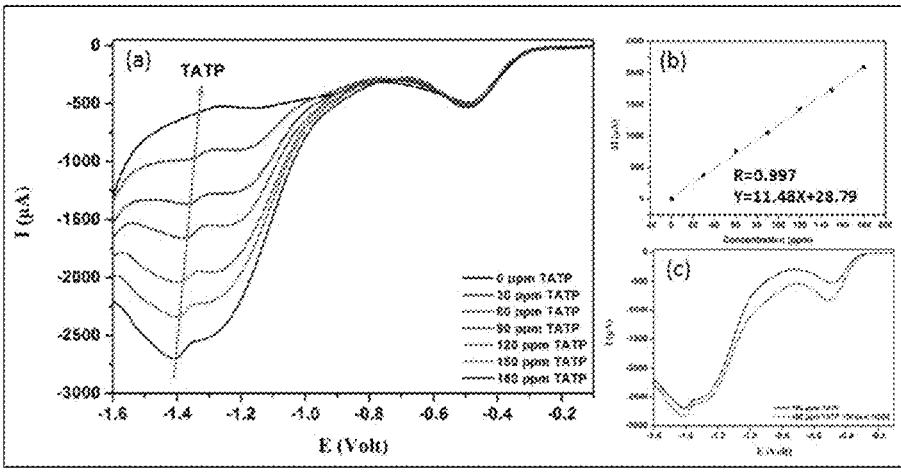
FIG. 5A
FIG. 5B
FIG. 5C

ELECTROCHEMICAL DETECTION OF PEROXIDE-CONTAINING COMPOUNDS

RELATED APPLICATIONS

This application claims the benefit of priority under 35 USC § 119(e) of U.S. Provisional Patent Application No. 62/519,977, filed Jun. 15, 2017, the contents of which are incorporated herein by reference in their entirety.

FIELD AND BACKGROUND OF THE INVENTION

The present invention, in some embodiments thereof, relates to detection of chemicals and, more particularly, but not exclusively, to electrodes, and to systems and methods employing same, usable in electrochemical detection of peroxide-based compounds such as peroxide-based explosives.

An 'explosive' is a chemically-unstable molecule having a rapid rate of autodecomposition, with the accompanying evolution of large amounts of heat and gaseous products. There has been a great increase in the development of trace and ultra-trace explosive detection in the last decade, mainly due to the globalization of terrorist acts, and the reclamation of contaminated land previously used for military purposes.

In addition, the availability of raw materials for the preparation of explosives, together with the growing access to information on preparing these explosives, allows for almost anyone with sufficient will and internet access to prepare a bomb. The vast number of people passing through borders, public places, airports etc. poses a huge challenge for current day security screening technologies. The same challenge applies to homes and buildings security. The ultimate goal is to be able to rapidly and effectively screen every passing person, without the need to delay the traffic of people, and without human contact if possible.

Explosives, especially concealed ones, have a very low vapor pressure or 'signature' in the surrounding air. The effective vapor pressure of explosives can be reduced by a factor of up to 1000, with the use of plastic packages. Detection methods for traces of explosives therefore continue to be plagued by the low volatility of many target analytes.

One of the most commonly-used high explosives over the last 100 years is 2,4,6-trinitrotoluene (TNT), which poses not only a direct security threat, but also great environmental concern due to soil and water contamination near production, storage and test sites. Other nitro-based explosives are also in use.

Peroxides-based explosives (e.g., cyclic organic peroxides) have also been used recently to build improvised explosive devices, increasing worldwide the awareness thereto. Development of methodologies for the detection of triacetone triperoxide (TATP), hexamethylene triperoxide diamine (HMTD), tetramethylene diperoxide dicarbamide (TMDD) and other cyclic organic peroxides have become an urgent priority. Most organic peroxides are explosive, and some compounds can be easily synthesized by mixing common commercial products such as acetone, hydrogen peroxide and strong acids. Most of the current technology in use for trace detection of explosives is unable to detect peroxide-based explosives [Oxley et al. *Propellants, Explosives, Pyrotechnics* 34, 539-543 (2009); Önnerud, H., Wallin, S. & Östmark, H. in *Intelligence and Security Informatics Conference (EISIC)*, 2011 European. 238-243 (IEEE)].

Past theoretical studies have showed a plausible approach based on the formation of complexes between the molecular ring structures of cyclic organic peroxide explosives and a central metal moiety, analogous to the formation of clatherates and crown ethers that selectively bind to ionic species in solution. These studies have predicted that TATP molecules can bind to several ions of different valency, with $In^{3+}$, $Zn^{2+}$ and $Ti^{4+}$ showing the highest binding energy [Dubnikova, F., Kosloff, R., Zeiri, Y. & Karpas, Z. *The Journal of Physical Chemistry A* 106, 4951-4956 (2002)].

Analytical procedures in use today for the trace detection of explosives typically involve collecting vapor samples and analyzing them with a sensitive method. Several methodologies have been reported for detecting TNT and other nitro-based explosives. These are based on electrochemistry, ion-mobility spectrometry, gas chromatography, high-performance liquid chromatography, surface enhanced Raman spectroscopy, nuclear quadrupole resonance, neutron activation analysis, photoluminescence, surface acoustic-wave devices, microcantilevers, fluorescent polymers, surface plasmon resonance, quartz crystal microbalance, immunosensors and other methods. These methods are reliable for explosives detection, but involve time-consuming procedures, high costs and operation by well qualified staff, which limits their application in field conditions.

Additional methods involve trained animals including dogs, mice and bees and utilize their highly sensitive sense of smell for traces explosive detection. These methods however require intense and expensive training of the animal, and handling by an expert.

While a large number of techniques are reported for the detection of nitro based explosives such as TNT, detection of peroxide-based explosives is more complicated. For example, while several detection methodologies rely on the chromophoric nitro groups present in TNT, peroxide-based explosive typically lack chromophoric groups.

Several direct methods for detection of peroxide-based explosives have been reported, including, for example, mass spectrometry, liquid chromatography-mass spectrometry, gas chromatography-mass spectrometry, Ion-mobility spectrometry-mass spectrometry and high-performance liquid chromatography. See, for example, Cotte-Rodriguez et al. *Chemical Communications*, 953-955, doi:10.1039/b515122h (2006); Widmer et al. *Analyst* 127, 1627-1632, doi:10.1039/b208350g (2002); Sigman et al. *Rapid Communications in Mass Spectrometry* 20, 2851-2857, doi:10.1002/rcm.2678 (2006); Buttigieg et al. *Forensic Science International* 135, 53-59 (2003); and Schulte-Ladbeck, R. & Karst, U. *Analytica Chimica Acta* 482, 183-188 (2003).

However, these methods suffer from relatively high costs, extensive operator skills, and limited field portability.

A few methods for a rapid detection of peroxide-based explosives based on decomposition of these compounds to hydrogen peroxide in the presence of an acid or ultraviolet radiation and its detection by photometrical and electrochemical methods have also been suggested. See, for example, Schulte-Ladbeck, et al. *Analytical Chemistry* 75, 731-735, doi:Doi 10.1021/Ac020392n (2003); Schulte-Ladbeck, R. & Karst, U. *Analytica Chimica Acta* 482, 183-188 (2003); Schulte-Ladbeck et al. *Analyst* 127, 1152-1154, doi:Doi 10.1039/B206673b (2002); Munoz et al. *Analyst* 132, 560-565, doi:Doi 10.1039/B701356f (2007); Lu et al. *Analyst* 131, 1279-1281, doi:Doi 10.1039/B613092e (2006); and Eren, S. et al. *Analyst* 135, 2085-2091, doi:Doi 10.1039/B925653a (2010).

Electrochemical detection methods utilize electrodes, immersed in an electrolyte, and connected to a potentiometer, which measure the current that flows between the electrodes upon potential application. Typically, during an electrochemical reaction the electrode potential is varied; and an electric current flows between the electrodes that is characteristic of the presence of an electrochemically reactive substance in the electrolyte. Electrochemical detection typically meets most of the above requirements of a robust and efficient methodology for detection of explosives. See, Caygill, J. S., Davis, F. & Higson, S. P. J. Current trends in explosive detection techniques. *Talanta* 88, 14-29, doi:DOI 10.1016/j.talanta.2011.11.043 (2012); Wang, J. Electrochemical sensing of explosives. *Electroanal* 19, 415-423, doi:DOI 10.1002/elan.200603748 (2007).

Most electrochemical methods for peroxide-based explosives detection rely on the detection of $H_2O_2$ formed from the acid or ultraviolet decomposition of the explosive material. Prussian-blue and $Fe^{II/III}$ ethylenediaminetetraacetate are examples of chemical modifications on a working electrode that are used in those methods. Additional examples include electrochemical detection of TATP performed by redox reaction with bromide ion at 55° C. Acetone and bromine, obtained in such a reaction, interact to give acetone bromides, such that a lack of free bromine is indicative of the presence of the explosive. Another example is the detection of HMTD using electro-generated chemiluminescence (ECL), while utilizing the tertiary amine moieties present in HMTD. See, for example, Schulte-Ladbeck et al. *Analyst* 127, 1152-1154, doi:Doi 10.1039/B206673b (2002); Lu et al. *Analyst* 131, 1279-1281, doi:Doi 10.1039/B613092e (2006); Laine et al. *Analytica Chimica Acta* 608, 56-60, doi:DOI 10.1016/j.aca.2007.12.003 (2008); Laine et al. *Microchem J* 91, 78-81, doi:DOI 10.1016/j.microc.2008.08.005 (2009); Zhao et al. *Journal of Electroanalytical Chemistry* 379, 501-503, doi:Doi 10.1016/0022-0728 (94)87175-2 (1994); Xie, Y. Q. & Cheng, I. F., *Microchem J* 94, 166-170, doi:DOI 10.1016/j.microc.2009.10.016 (2010); Parajuli, S. & Miao, W. J., *Analytical Chemistry* 81, 5267-5272, doi:Doi 10.1021/Ac900489a (2009).

One of the most pronounced limitations in electrochemical measurement under atmospheric conditions is the presence of dissolved oxygen in a sample. The dissolved oxygen concentration in aqueous electrochemical solution is about 0.25 mM (about 8 ppm) [Julia, P. L. C. & Coso, E. B. *Homenatge professor Josep M. Costa (eBooK)* 2a part. *Trends in electrochemistry and corrosion at the beginning of the 21st century.* (Publicacions i Edicions de la Universitat de Barcelona, 2004)] and is much higher in non-aqueous electrochemical solutions [Achord, J. M. & Hussey, *Analytical Chemistry* 52, 601-602, (1980)]. The oxygen is reduced practically at the same potentials as peroxides-based explosives, and, since oxygen concentration is higher by several orders of magnitude than that of the explosive traces, signals generated by the peroxide-based explosives traces are substantially masked. This limitation is typically treated by deaeration; the oxygen is removed by means of bubbling inert gas, for example argon or nitrogen. Typically, 10-15 minutes of deaeration are required in order to obtain efficient oxygen removal in a sample of approximately 5 ml. This lengthy procedure is not in line with the requirements for real time detection of nitro-containing explosives [W. Chen, Y. Wang, C. Bruckner, C. M. Li, Y. Lei, *Sensor Actuat B-Chem* 2010, 147. 191-197].

In addition, a major overlap of the reduction peak of traces of $H_2O_2$, which may be found in field conditions, and that of a peroxide-based explosive further complicate the electrochemical detection, often leading to "false positive" detection. See, for example, Butler et al. *Talanta* 41, 211-215, (1994); Marinović et al. *Journal of Electroanalytical Chemistry* 648, 1-7, (2010).

WO 2011/154939 describes nanodevices which utilize functionalized nanowires for detecting nitro-containing compounds. The nanowires feature a functional moiety that interacts with a nitro-containing compound by forming a charge-transfer complex therewith.

WO 2005/050157, WO 2006/090401, and WO 2007/029245 teach systems for detecting traces of nitro-aromatic compounds in air, which utilize carbon electrodes modified by amino-aromatic compound or nitrogen-containing heterocyclic compounds.

WO 2014/111944 describes nanodevices which utilize functionalized nanowires for detecting peroxide-based and/or nitro-containing explosives.

Additional background art includes Spalek ET AL. *J Chem Soc Farad T 1* 78, 2349-2359, doi:Doi 10.1039/F19827802349 (1982); Weiss, *J. Transactions of the Faraday Society* 31, 1547-1557 (1935); Sheppard, S. A. et al. *Analyst* 123, 1923-1929, doi:Doi 10.1039/A803310b (1998); and Chaki et al. *Chemical Communications*, 76-77, doi:Doi 10.1039/B107965b (2002).

Yet additional background art includes Chaubey, A. & Malhotra, B. D. Mediated biosensors. *Biosens Bioelectron* 17, 441-456, (2002); Zang et al. *Analytica Chimica Acta* 683, 187-191, (2011); U.S. Pat. No. 6,872,786; Chen et al. *Sensor Actuat B-Chem* 147, 191-197, (2010); Filanovsky, B. et al. *Adv Funct Mater* 17, 1487-1492, (2007); Grigoriants, I. et al. *Electrochim Acta* 54, 690-697, (2008); Guo et al. *Electroanal* 23, 885-893, (2011); Chen et al. *Chemistry—An Asian Journal* 6, 1210-1216, (2011); Wang et al. *Sensors-Basel* 11, 7763-7772, (2011); Cizek, K. et al. *Analytica Chimica Acta* 661, 117-121, (2010); Galik et al. *Electroanal* 23, 1193-1204, doi:DOI 10.1002/elan.201000754 (2011); WO 2010/112546; WO 2010/227382; WO 2015/059704; WO 2017/098518; Engel, Y. et al. *Angew Chem Int Edit* 49, 6830-6835, (2010); Dwivedy et al. *Journal of Chromatography A* 29, 120-125 (1967); and Lichtenstein, A. et al. *Nat Commun* 5, (2014).

SUMMARY OF THE INVENTION

The present inventors have now designed and successfully practiced a novel sensing system for electrochemical detection of peroxide-containing compounds. The designed system can perform electrochemical detection of trace amounts of peroxide-containing explosives efficiently in the presence of one or both hydrogen peroxide and dissolved oxygen in a single measurement. The sensing system can be operated such that detectable concentration of a peroxide-containing compound is lower than 500 ppb and even lower, and at a detection time of less than 20 seconds, and is therefore highly useful in field conditions.

The sensing system disclosed herein is based on a carbon electrode, preferably a carbon fiber electrode, more preferably, a carbon fiber microelectrode, modified at its surface by absorbing thereto ions of a metal that promotes peroxide decomposition, optionally together with an ion-permeable material.

The sensing system and methods disclosed herein meet the requirements of a sensitive and robust methodology for detection of explosives by being highly sensitive, selective (sophisticated) and working in real time regime, while at the same time, it features a high sampling rate and multiplex capabilities, while maintaining handling simplicity and reliability. The sensing system disclosed herein can be designed as hand held devices, with minimized and miniaturized dimensions, weight and costs.

According to an aspect of some embodiments of the present invention there is provided a sensing electrode comprising a carbon electrode and a functional moiety being in association with (e.g., attached or absorbed to) at least a portion of a surface of the electrode. According to some of any of the embodiments described herein, the functional moiety promotes decomposition of hydrogen peroxide.

According to an aspect of some embodiments of the present invention there is provided a sensing electrode comprising a carbon electrode and a plurality of functional moieties being in association with (e.g., attached to absorbed to) at least a portion of a surface of the electrode. According to some of any of the embodiments described herein, the functional moiety promotes decomposition of hydrogen peroxide.

According to some of any of the embodiments of the present invention there is provided a sensing electrode comprising a carbon electrode and a functional moiety being is association with (e.g., attached or absorbed to) at least a portion of a surface of the electrode, the functional moiety comprising at least one metal species that promotes decomposition of hydrogen peroxide.

According to some of any of the embodiments described herein, the functional moiety is absorbed to at least a portion of the surface of the electrode.

According to some of any of the embodiments described herein, the carbon electrode is a carbon fiber electrode.

According to some of any of the embodiments described herein, the electrode is a carbon fiber microelectrode.

According to some of any of the embodiments described herein, the electrode is a carbon paper microelectrode.

According to some of any of the embodiments described herein, the carbon electrode is a gas-permeable carbon electrode, for example, a gas permeable carbon paper microelectrode or a gas-permeable carbon fabric electrode, or a gas permeable carbon fiber electrode.

According to some of any of the embodiments described herein, the metal species is selected from elemental metal, a metal oxide, a metal ion, and an organometallic complex of any of the foregoing.

According to some of any of the embodiments described herein, the metal species is selected from elemental metal, a metal oxide and a metal ion.

According to some of any of the embodiments described herein, the functional moiety comprises metal ions.

According to some of any of the embodiments described herein, the metal ions undergo reduction to thereby provide metal particles, upon application of a potential in a range of from about −0.05 to about 2 volts.

According to some of any of the embodiments described herein, the functional moiety further comprises particles of the metal (e.g., of elemental metal).

According to some of any of the embodiments described herein, an amount of the particles of the metal is less than 70 mol %, or less than 65 mol %, of the total number of moles of the metal in the functional moiety.

According to some of any of the embodiments described herein, a mol ratio of the metal ions and the particles of the metal ranges from 70:30 to 30:70.

According to some of any of the embodiments described herein, the metal is selected from silver, rhodium, palladium, iridium, gold, platinum, iron, copper, hafnium, manganese, iridium, gadolinium, cerium, lead, and bismuth.

According to some of any of the embodiments described herein, the metal is silver.

According to some of any of the embodiments described herein, the functional moiety comprises at least one metal species having an organic moiety associated therewith.

According to some of any of the embodiments described herein, at least one metal species having an organic moiety associated therewith is selected from an organic salt of the metal, and an organometallic complex of the metal and an organometallic complex of an oxide of the metal.

According to some of any of the embodiments described herein, at least one metal species having an organic moiety associated therewith is an organic salt of the metal, comprising a metal ion and an organic anion.

According to some of any of the embodiments described herein, the metal is silver and the organic salt of the metal is silver benzoate.

According to some of any of the embodiments described herein, the electrode further comprises an ion-permeable material absorbed to the surface.

According to some of any of the embodiments described herein, the ion-permeable material comprises a polymeric film.

According to some of any of the embodiments described herein, the ion-permeable material is or comprises Nafion®.

According to some of any of the embodiments described herein, the functional moiety physically interacts with the ion-permeable material.

According to some of any of the embodiments described herein, the electrode comprises an organic salt of the metal and the polymeric film absorbed to the surface.

According to some of any of the embodiments described herein, the electrode is usable for determining a presence and/or level of a peroxide-containing compound in a sample.

According to an aspect of some embodiments of the present invention there is provided a sensing system comprising a sensing electrode according to any of the respective embodiments and any combination thereof, the sensing electrode being connectable to a power source.

According to some of any of the embodiments described herein, the sensing electrode forms a part of an electrochemical cell.

According to some of any of the embodiments described herein, the electrochemical cell further comprises a reference electrode.

According to some of any of the embodiments described herein, the electrochemical cell further comprises an auxiliary electrode.

According to some of any of the embodiments described herein, the system is operable upon contacting the sensing electrode with an electrolyte.

According to some of any of the embodiments described herein, the electrochemical cell further comprises an inlet port or any other means for introducing the electrolyte solution.

According to some of any of the embodiments described herein, the electrochemical cell further comprises an electrolyte, and wherein at least a portion of the sensing electrode contacts the electrolyte.

According to some of any of the embodiments described herein, the electrolyte features an alkaline pH.

According to some of any of the embodiments described herein, the electrolyte comprises a mixture of an aqueous solvent and an organic solvent.

According to some of any of the embodiments described herein, the electrolyte comprises a quaternary ammonium salt.

According to some of any of the embodiments described herein, the system further comprises a sample inlet or any other means for contacting the sample with the sensing electrode.

According to some of any of the embodiments described herein, the system further comprises a sample inlet or any other means for introducing a sample to the electrochemical cell.

According to some of any of the embodiments described herein, the system further comprises a gas outlet.

According to some of any of the embodiments described herein, the system is devoid of means for deaerating the electrochemical cell prior to contacting the system with a sample.

According to some of any of the embodiments described herein, the electrochemical cell further comprises a power source electrically connected to the sensing electrode.

According to some of any of the embodiments described herein, the system further comprises a device for measuring an electrochemical parameter of the sensing electrode.

According to some of any of the embodiments described herein, the system further comprises an electrical current measuring device for measuring an electrical current or a change in an electrical current generated at the sensing electrode.

According to some of any of the embodiments described herein, the power source is configured to apply a varying potential to the sensing electrode.

According to some of any of the embodiments described herein, the system further comprises a device for determining a change in the electrical current in response to the varying potential.

According to some of any of the embodiments described herein, the system is configured such that upon application of a potential, a portion of the metal species is in a form of metal particles, the portion being no more than 70 mol % of the total amount of the metal species.

According to some of any of the embodiments described herein, the functional moiety comprises metal ions and wherein upon application of a potential, a portion of the metal ions is converted into the metal particles, the portion being no more than 50 mol % of the amount of the metal ions.

According to some of any of the embodiments described herein, the functional moiety comprises particles of a metal and ions of the metal, the system being configured such that upon application of a potential, a mol ratio of the ions of the metal and the particles of the metal ranges from 75:25 to 25:75.

According to some of any of the embodiments described herein, the electrochemical cell is configured such that upon contacting a sample containing a peroxide-containing compound with the sensing electrode, a presence and/or level of an electrochemical parameter generated in response to applying potential to the sensing electrode is indicative of a presence and/or level of the peroxide-containing compound.

According to some of any of the embodiments described herein, the system is configured for determining a change in the electrical current in response to a varying potential applied to the sensing electrode, the change being indicative of a presence and/or level of the peroxide-containing compound.

According to some of any of the embodiments described herein, the system further comprises a data processor configured to determine a level of the peroxide-containing compound in a sample, the determining being using at least one of (i) a calibration curve stored on a computer readable medium, (ii) a lookup table stored on a computer readable medium, and (iii) a predetermined relationship between a current generated by the peroxide-containing compound and the level.

According to some of any of the embodiments described herein, the predetermined relationship comprises a linear relationship.

According to an aspect of some embodiments of the present invention there is provided a method of detecting a peroxide-containing compound in a sample, the method comprising:

contacting the sample with a sensing electrode according to any of the respective embodiments and any combination thereof;

applying a potential to the sensing electrode; and measuring an electrochemical parameter of the sensing electrode, wherein a presence and/or level of the parameter is indicative of a presence and/or level of the peroxide-containing compound in the sample.

According to some of any of the embodiments described herein, contacting the sensing electrode with the sample comprises introducing the sample to a sensing system according to any of the present embodiments (e.g., by means of an air pump).

According to some of any of the embodiments described herein, the electrochemical parameter comprises an electrical current generated at the sensing electrode, wherein a presence and/or level of the electrical current is indicative of a presence and/or level of the peroxide-containing compound.

According to some of any of the embodiments described herein, contacting the sample with the sensing electrode comprises contacting an electrolyte solution comprising the sample with the sensing electrode.

According to some of any of the embodiments described herein, the method is devoid of deaerating the system.

According to some of any of the embodiments described herein, the sample is a fluid sample.

According to some of any of the embodiments described herein, the sample comprises oxygen.

According to some of any of the embodiments described herein, a concentration of dissolved oxygen in the electrolyte is at least 1 ppm.

According to some of any of the embodiments described herein, a detectable concentration of the peroxide-containing compound in the sample is lower than 1 micromolar.

According to some of any of the embodiments described herein, applying the potential is performed by linear sweep voltammetry.

According to some of any of the embodiments described herein, the method further comprises, prior to introducing the sample, repetitively applying the potential for at least 5 consecutive times.

According to some of any of the embodiments described herein, repetitively applying the potential is performed such that a portion of the metal species is converted to metal particles, the portion being no more than 50 mol % of the total amount of the metal species.

According to some of any of the embodiments described herein, repetitively applying the potential is performed such that the electrode comprises no more than 70 mol % of metal species which are metal particles, of the total amount of the metal in the functional moiety.

According to some of any of the embodiments described herein, the functional moiety comprises particles of a metal and ions of the metal, and wherein the repetitively applying the potential is performed such that a mol ratio of the ions and the particles ranges from 75:25 to 25:75.

According to some of any of the embodiments described herein, the peroxide-containing compound is a peroxide-containing explosive.

According to some of any of the embodiments described herein, the explosive is selected from the group consisting of TATP, HMDT and TMDD.

According to some of any of the embodiments described herein, the sample further comprises hydrogen peroxide.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

Implementation of the method and/or system of embodiments of the invention can involve performing or completing selected tasks manually, automatically, or a combination thereof. Moreover, according to actual instrumentation and equipment of the method and/or system of the invention, several selected tasks could be implemented by hardware, by software or by firmware or by a combination thereof using an operating system.

For example, hardware for performing selected tasks according to embodiments of the invention could be implemented as a chip or a circuit. As software, selected tasks according to embodiments of the invention could be implemented as a plurality of software instructions being executed by a computer using any suitable operating system. In an exemplary embodiment of the invention, one or more tasks according to exemplary embodiments of method and/or system as described herein are performed by a data processor, such as a computing platform for executing a plurality of instructions. Optionally, the data processor includes a volatile memory for storing instructions and/or data and/or a non-volatile storage, for example, a magnetic hard-disk and/or removable media, for storing instructions and/or data. Optionally, a network connection is provided as well. A display and/or a user input device such as a keyboard or mouse are optionally provided as well.

BRIEF DESCRIPTION OF THE SEVERAL VIEWS OF THE DRAWING(S)

The patent or application file contains at least one drawing executed in color. Copies of this patent or patent application publication with color drawing(s) will be provided by the Office upon request and payment of the necessary fee.

Some embodiments of the invention are herein described, by way of example only, with reference to the accompanying drawings. With specific reference now to the drawings in detail, it is stressed that the particulars shown are by way of example and for purposes of illustrative discussion of embodiments of the invention. In this regard, the description taken with the drawings makes apparent to those skilled in the art how embodiments of the invention may be practiced.

In the drawings:

FIG. 1 presents linear sweep voltammetry curves (obtained at a scan rate of 0.1 volt/second) of non-modified CF microelectrode in the presence of an electrolyte solution containing a mixture of NaOH in deionized water (pH=12) and acetonitrile at 7:3 volume ratio and 0.1 M $TBABF_4$, without TATP addition (black line), upon addition of 20, 40 and 60 ppm of TATP (red, blue and turquoise lines, respectively), and upon addition of 60 ppm TATP and 40 ppm $H_2O_2$ (pink line).

FIGS. 2A-C present linear sweep voltammetry curves (obtained at a scan rate of 0.1 volt/second) of silver benzoate-modified CF microelectrode in the presence of an electrolyte solution containing a mixture of NaOH in deionized water (pH=12) and acetonitrile at 7:3 volume ratio and 0.1 M $TBABF_4$, without HMDT addition (black line), and upon addition of HMDT at the indicated concentrations (FIG. 2A), and upon addition of 180 ppm HMTD and 180 ppm HMTD and 40 ppm $H_2O_2$ (black and redlines, respectively, in FIG. 2C); The green arrow in FIG. 2A represents the current peaks of HMTD that were used for the calibration curve (FIG. 2B; $\Delta I$=background current–current peak of HMTD.

FIGS. 3A-C present scanning electron microscope (secondary electrons (SE) and backscattered electrons (BSE) images (right panels) and X-ray photoelectron spectroscopy atomic concentrations (left images) of an unmodified CF microelectrode (FIG. 3A), and of a silver benzoate-modified CF microelectrode after performing one linear sweep voltammetry scan from 0 volts to −1.6 volts in the electrolyte solution (FIG. 3B) and after performing 100 linear sweep voltammetry scans from 0 volts to −1.6 volts in the electrolyte solution (FIG. 3C).

FIGS. 4A-C present linear sweep voltammetry curves (obtained at a scan rate of 0.1 volt/second) of silver benzoate-modified CF microelectrode in the presence of an electrolyte solution containing a mixture of NaOH in deionized water (pH=12) and acetonitrile at 7:3 volume ratio and 0.1 M $TBABF_4$, performed following 15 subsequent repetitions of linear sweep voltammetry scans from 0 volts to −1.6 volts, without HMDT addition (black line), and upon addition of HMDT at the indicated concentrations (FIG. 4A), and upon addition of 150 ppm HMDT and 150 ppm HMDT and 40 ppm $H_2O_2$ (black and redlines, respectively, in FIG. 4C); The green arrow in FIG. 4A represents the current peaks of HMTD that were used for the calibration curve (FIG. 4B; $\Delta I$=background current–current peak of HMTD.

FIGS. 5A-C present linear sweep voltammetry curves (obtained at a scan rate of 0.1 volt/second) of silver benzoate-modified CF microelectrode in the presence of an electrolyte solution containing a mixture of NaOH in deionized water (pH=12) and acetonitrile at 7:3 volume ratio and 0.1 M $TBABF_4$, performed following 15 subsequent repetitions of linear sweep voltammetry scans from 0 volts to −1.6 volts, without TATP addition (black line), and upon addition of TATP at the indicated concentrations (FIG. 4A), and upon addition of 150 ppm TAPT and 150 ppm HMTD and 30 ppm $H_2O_2$ (black and redlines, respectively, in FIG. 4C); The green arrow in FIG. 4A represents the current peaks of TAPT that were used for the calibration curve (FIG. 4B; $\Delta I$=background current–current peak of TAPT).

Figure 6:
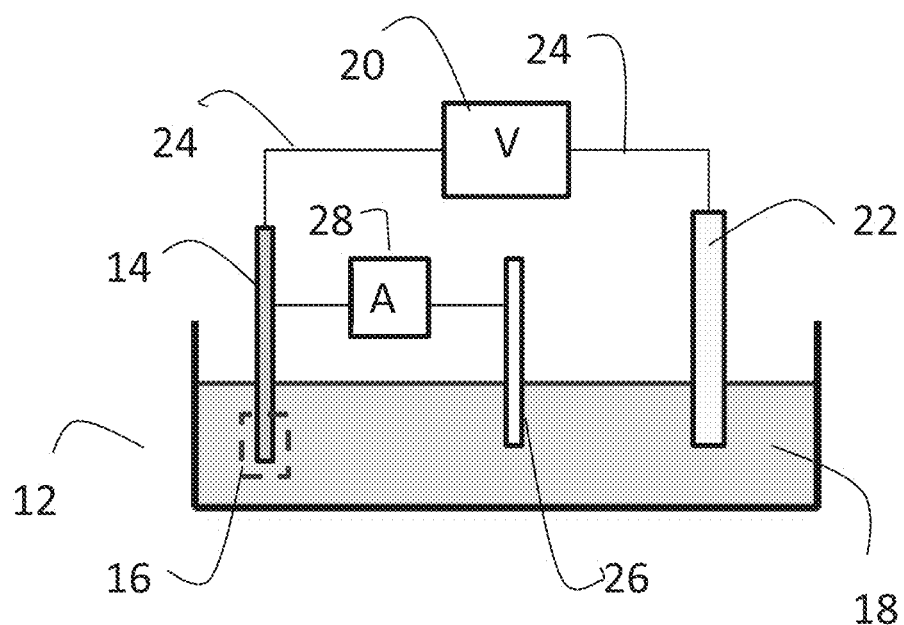

FIG. 6 presents a schematic illustration of an exemplary electrochemical cell according to some embodiments of the present invention.

Figure 7:
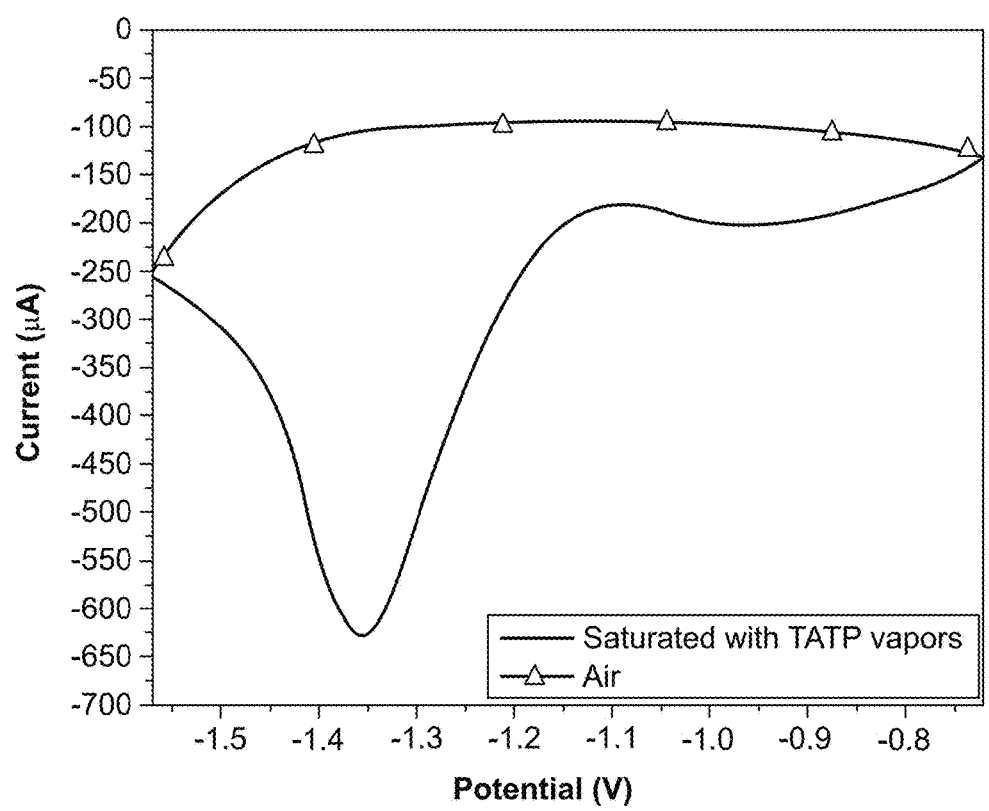

FIG. 7 presents linear sweep voltammetry curves (obtained at a scan rate of 0.1 volt/second) of a modified CF microelectrode according to exemplary embodiments of the present invention, in the presence of an electrolyte solution containing a mixture of NaOH in deionized water (pH=12) and acetonitrile at 7:3 volume ratio and 0.1 M $TBABF_4$, in the presence of air (black line) and in the presence of a gaseous sample saturated with vapors of TATP (red line).

DESCRIPTION OF SPECIFIC EMBODIMENTS OF THE INVENTION

The present invention, in some embodiments thereof, relates to detection of chemicals and, more particularly, but not exclusively, to electrodes, and to systems and methods employing same, usable in electrochemical detection of peroxide-based compounds such as peroxide-based explosives.

Before explaining at least one embodiment of the invention in detail, it is to be understood that the invention is not necessarily limited in its application to the details of construction and the arrangement of the components and/or methods set forth in the following description and/or illustrated in the drawings and/or the Examples. The invention is capable of other embodiments or of being practiced or carried out in various ways.

In a search for improved systems for electrochemical detection of peroxide-containing compounds, which feature enhanced selectivity and sensitivity while avoiding complicate and time-consuming procedures, the present inventors have recognized that a working electrode which is made of a flexible material that can be easily and stably modified, and which can be manipulated so as to optimize its surface, to thereby increase its sensitivity, is desirable.

The present inventors have particularly sought for a system that allows distinguishing between dissolved oxygen, hydrogen peroxide and other peroxide-containing compounds so as to perform electrochemical detection of peroxide-containing compounds in electrolyte solutions while overcoming the limitations in this methodology associated with the presence of dissolved oxygen and trace amounts of hydrogen peroxide. The present inventors have recognized that influencing the reduction peaks of oxygen without time-consuming steps (e.g., while circumventing the need to perform deaeration) can be effected by chemically modifying the surface of the working electrode.

While conceiving the present invention, the present inventors have considered utilizing carbon electrodes, due to the flexibility of carbon materials, and have particularly conceived carbon microfiber electrode as featuring a morphology that allows suitable signal-to-noise ratio, and which can potentially serve as effective, low cost and sensitive sensor element which meets the strict requirements of detection of explosive traces.

The present inventors have conceived that performing chemical decomposition of peroxides on the surface of a carbon electrode, while utilizing a catalyst of such decomposition, would achieve the above-mentioned goals.

As demonstrated in the Examples section that follows, the present inventors have indeed designed an electrochemical system which allows sensitive and selective detection of exemplary peroxide-containing explosives, TATP and HMTD, also in the presence of hydrogen peroxide. The electrochemical system exhibits high sensitivity, allows detecting peroxide-containing compounds at a concentration as low as 250 ppb, allows performing real-time and continuous monitoring of peroxide-containing compounds, is operated by rapid procedures, while avoiding time consuming processes of purification and pre-concentration, allows detection within less than seconds, is free of a labeling agent, and thereby circumvents the need to use excitation and imaging techniques, is easy to integrate with a lab on chip system/electrochemical system, can be operated with small volume sample; is reusable; and uses low-cost and low-energy constructions and operation.

The designed electrochemical system, by being capable of efficiently detecting peroxide-containing compounds in the presence of dissolved oxygen and/or hydrogen peroxide, can be utilized, for example, in aqueous environments such as sea water, and in containers, open fields, and any other oxygen-containing environments.

The system can be configured so to feature minimized dimensions, efficient and user-friendly delivery means for introducing the sample to the system, at the user interface.

Referring now to the drawings, FIG. 6 presents a schematic illustration of an exemplary set up of an electrochemical cell according to some embodiments of the present invention.

FIG. 1 presents data obtained in linear sweep voltammetry using a non-modified carbon microfiber electrode and show non-separable reduction peaks observed for TAPT and hydrogen peroxide, and for dissolved oxygen.

FIGS. 2A-C, 4A-C and 5A-C present data obtained in linear sweep voltammetry using a silver-modified carbon fiber microelectrode according to some embodiments of the present invention, and show the separate reduction peaks observed for TAPT or HMDT, hydrogen peroxide, and dissolved oxygen.

FIG. 7 presents data obtained in linear sweep voltammetry using a silver-modified carbon fiber microelectrode according to some embodiments of the present invention and gaseous sample of TATP, and show the pronounced reduction peak obtained.

FIGS. 3A-C presents SEM and XPS measurements of a non-modified CF electrode and of a silver-modified electrode after one and 100 voltammetry cycles, and show a formation of silver nanoparticles on the electrode-surface upon potential application. As demonstrated in the Examples section that follows, it has been shown that efficient detection of peroxides is effected upon transformation (conversion) of a portion of the silver ions to silver nanoparticles, which is afforded by running several repetitive voltammetry cycles prior to introducing a sample to the system.

These data clearly demonstrate that an electrochemical system according to the present embodiments enables to perform sensitive, selective, multiplex and high sampling rate detection of peroxide-containing compounds such as peroxide-containing explosives.

Embodiments of the present invention therefore provide an improved sensing electrode, and an electrochemical system and method utilizing same for detecting peroxide-containing compounds in a sample, which are particularly usable in detecting peroxide-containing compounds in the presence of dissolved oxygen.

Sensing Electrode:

A sensing electrode according to embodiments of the present invention comprises a carbon electrode and a functional moiety in association with at least a portion of a surface of the electrode, the functional moiety being such that promotes decomposition (e.g., chemical or electrochemical decomposition) of hydrogen peroxide.

According to some embodiments of the present invention, the carbon electrode features at least one nanoscale or microscale dimension.

By "microscale dimension" it is meant that at least one dimension of the electrode is lower than 1 mm, or ranges from 0.1 micron to 900 microns.

By "nanoscale dimension" it is meant that at least one dimension of the electrode is lower than 1 micron, or ranges from 0.1 nanometer to 900 nanometers.

The nanoscale or microscale dimension depends on the shape of the electrode. If an electrode is generally shaped as a cylinder, the at least one dimension can be one or both of a length and a diameter of the electrode. If the electrode is generally shaped as a rectangular, the at least one dimension can be one or more of a length and a width of the electrode.

Electrodes featuring one or more microscale or nanoscale dimension(s) are also referred to herein and in the art as microelectrodes.

Carbon electrodes or microelectrodes can be made of glassy carbon, screen-printed carbon, carbon films, carbon fibers, carbon paste, carbon nanoubes, and others.

According to some embodiments of the present invention, the carbon electrode is a carbon fiber electrode, or a carbon fiber microelectrode (also referred to herein interchangeably as "carbon microfiber electrode").

A carbon fiber (CF) electrode is an electrode that comprises elementary carbon (e.g., graphite) shaped as a fibrous structure (e.g., a filament). Generally, but not necessarily, a CF electrode features a microscale or even nanosclae diameter or thickness, typically, but not limited to, in a range of from 1 to 500 microns, or from 5 to 200 microns, or from 5 to 100 microns, or from 5 to 50 microns or from 5 to 20 microns. Generally, but not necessarily, a CF electrode features a length (height) of from about 100 microns to about 50 mm, or from about 100 microns to about 1 mm, or from about 100 microns to about 800 microns, including any intermediate values and subranges therebetween. CF electrode featuring at least one dimension in the microscale or nanoscale range is a CF microelectrode.

In some embodiments the CF microelectrode further comprises a mechanical support enveloping or surrounding at least a portion of the electrode, leaving a protruding tip of e.g., from 10 to 100 microns, of unsupported, exposed portion of the electrode.

The CF microelectrode can be a single-barrel or a multi-barrel electrode.

In some embodiments, a CF microelectrode is a gas-permeable electrode. Gas permeable electrodes allow sensing of gaseous samples (e.g., air) and/or analytes while circumventing the need to introduce the sample via a dedicated gas inlet.

By "gas-permeable" it is meant that the electrode is characterized by air permeability through plane higher than 0.3 cfm/ft$^2$ through 0.25 mm, when measured according to standard assays such as ASTM 737-96, ISO 5636, ISO 4638, ISO 9237, and TAPPI T460.

The CF microelectrodes can be carbon fabric electrodes or carbon paper electrodes. Carbon fabric electrodes can be made of woven or non-woven carbon filaments or bundles of filaments. Both electrode types are preferably gas-permeable electrodes.

Exemplary commercially available gas-permeable carbon fabric microelectrodes that are usable in the context of the present embodiments include, but are not limited to, plain carbon cloth such as, for example, electrodes marketed as ELAT—Hydrophilic Plain Cloth®, 1071 HCB plain carbon cloth, Panex 30®.

Exemplary commercially available gas-permeable carbon paper microelectrodes that are usable in the context of the present embodiments include, but are not limited to, electrodes marketed by Freudenberg FCCT, such as Freudenberg H23, electrodes of the Spectracarb™ family, Sigracet 39 AA, electrodes marketed under the trade name AvCarb® (e.g., AvCarb P75), and similar gas-permeable carbon paper electrodes.

Any commercially available CF microelectrode can serve as a raw material for providing a CF microelectrode according to the present embodiments, upon generating on at least a part of its surface a functional moiety as described herein.

In some of any of the embodiments described herein, a CF microelectrode is a carbon paper electrode.

In some of any of the embodiments described herein, the CF microelectrode (e.g., the carbon fiber microelectrode) is characterized by a surface area of at least 10-50 cm$^2$ per geometrical cm$^2$, including any intermediate value and subranges therebetween. In some embodiments, the CF microelectrode is electrically connectable to other parts of a sensing system via electrically conducting wires, for example, conducting metal foils such as, but not limited to, Ni foils.

The CF microelectrode of the present embodiments features a functional moiety, or a plurality of functional moieties, as described herein in any of the respective embodiments, in association with at least a portion of its surface (e.g., an exposed portion of the electrode's surface).

By "association with" or "being associated with" and grammatical diversions thereof, it is meant that the functional moiety or moieties are attached to at least a portion of the electrode's surface by physical and/or chemical means, including physical deposition, physical absorption and/or chemical absorption, for example, by means of physical entrapment or entanglement in or with the carbon fibers, and/or by means of hydrophobic interactions and/or hydrogen bond interactions and/or other chemical interactions.

In some of any of the embodiments described herein, the CF microelectrode features a plurality of functional moieties as described herein in association with at least a portion of its surface.

In some of any of the embodiments described herein, the functional moiety or moieties is/are absorbed to at least a portion of the electrode's surface.

As defined hereinabove, by "absorbed" it is meant that a functional moiety is attached to the surface by physical absorption and/or chemical absorption, for example, by means of physical entrapment or entanglement in or with the carbon fibers, and/or by means of hydrophobic interactions and/or hydrogen bond interactions and/or other chemical interactions with the carbon fibers.

In some of any of the embodiments described herein, the functional moiety is such that can participate in electrocatalytic reduction of peroxides.

In some of any of the embodiments described herein, the functional moiety promotes decomposition of peroxides by itself and/or is capable of generating (e.g., upon an electrochemical process) a moiety that promotes decomposition of peroxides.

As is known in the art, various metal-based materials, including, for example, silver (Ag), platinum (Pt), palladium (Pd), copper (Cu), iridium (Jr) and gold (Au), as well as iridium (Jr), iron (Fe), copper (Cu), hafnium (Hf), manganese (Mn), gadolinium (Gd), cerium (Ce), lead (Sb), and bismuth (Bi) and metal complexes, metal salts and/or metal oxides thereof, can participate in a catalytic decomposition of peroxides.

Some of the metal-based materials are active in decomposition of peroxides when in an elemental, metallic form, some metal-based materials are active when forming a part of a metal complex and/or a metal oxide and/or a metal salt, and some metal-based materials are active when a combination of elemental metal and a metal complex and/or metal ions and/or metal oxides is in contact with a peroxide.

Additional examples of metal-based materials that can participate in decomposition of peroxides include, but are not limited to, iron-based materials, such as $Fe_2O_3$ and organometallic complexes thereof, $CuO$, $HfO_2$, $CeO_2$, $Gd_2O_3$, manganese dioxide, cobalt oxide, lead oxide, as well as lead, bismuth, and manganese, including organometallic complexes of any of the foregoing.

In some of any of the embodiments described herein, the functional moiety comprises or is capable of generating, one or more metal species that promote(s) decomposition of peroxides (e.g., electric decomposition of peroxides).

By "metal species" it is meant any metal-containing species, including elemental metal in a form of, for example, powder, granules, flakes, plates and/or particles, including microparticles and nanoparticles; metal ions (typically cations) which form a part of a metal salt or of a metal complex; metal oxides; metallic complexes, including organometallic complexes, of a metal or of a metal ion or of a metal oxide; and any other metal-containing species.

In some of any of the embodiments described herein, the metal species comprises ions of a metal that promotes decomposition of peroxide, for example, electrocatalytic decomposition of peroxides.

In some of any of the embodiments described herein, the metal ions are such that undergo reduction to thereby provide elemental metal (e.g., in a form of particles), upon application of a potential in a range of from about 0.05 volt to about 2 volt.

Such metal ions generate, upon potential application, metal particles that promote (catalyze) decomposition of peroxides, and the overall electrochemical reaction can be referred to as electrocatalytic decomposition of peroxides.

Alternatively, the metal species is or comprises elemental metal, which promotes as such (as an elemental metal) decomposition of peroxides.

Further alternatively, the metal species is or comprises metals ions, which promote as such (as metal ions) decomposition of peroxides.

Further alternatively, the metal species is or comprises a metal oxide, which promotes as such (as a metal oxide) decomposition of peroxides or which can generate elemental metal (e.g., as metal particles) and/or metal ions, which promote(s) decomposition of peroxides (e.g., upon application of potential).

Further alternatively, the metal species is or comprises an organometallic complex which promotes as such decomposition of peroxides or which can generate elemental metal (e.g., as metal particles) and/or metal ions, which promote(s) decomposition of peroxides (e.g., upon application of potential).

The present inventors have shown that a functional moiety that comprises both particles of a metal that promotes decomposition of peroxides and ions of the same metal provides efficient electrochemical sensing of peroxides.

In some of any of the embodiments described herein, the functional moiety comprises both ions and particles of a metal that promotes decomposition of peroxides, as described herein.

In some of any of the embodiments described herein, the metal species comprises both ions and particles of a metal that promotes decomposition of peroxides, as described herein.

In some of any of the embodiments described herein, an amount of the metal particles is no more than 70 mol %, no more than 65 mol %, or no more than 40 mol % or no more than 30 mol %, of the total amount of the metal species in the functional moiety.

By "mol %" in the context of these embodiments it is meant the number of moles of the metal when in a form of elemental metal particles, divided by the total number of moles of the metal species, that is, the sum of the moles of the metal atoms in the functional moiety, namely, the sum of both metal ions and elemental metal particles, multiplied by 100.

Generally, by "mol %" it is meant herein the number of moles of a metal species, divided by the total number of moles of the metal atoms, that is, the sum of the moles of the metal species in the functional moiety, multiplied by 100. The term "mol %" can also be referred to as "atomic concentration".

In some of any of the embodiments described herein, an amount of the metal particles is from about 5 mol % to about 65 mol %, of the total amount of the metal species in the functional moiety (e.g., total number of moles of both metal ions and metal particles), including any intermediate values and subranges therebetween.

By "elemental metal" it is meant a metal in its elemental form, that is, a metal species that consists solely of atoms of the metal element. In some embodiments, the elemental metal features a zero net charge.

In some embodiments, the metal species or the functional moiety comprising same comprises particles of a metal (e.g., elemental metal) and ions of a metal (e.g., derived from a metal salt, a metal oxide or a metal complex), and in some of these embodiments, a mol ratio of the metal ions and the metal particles ranges from 75:25 to 25:75, and can be, for example, 75:25, 72:28, 70:30, 68:32, 65:35, 62:38, 60:40, 58:42, 55:45, 52:48, 50:50, 48:52, 45:55, 42:58, 40:60 38:62, 35:65, 32:68, 30:70, 28:72 or 25:75, including any intermediate values and subranges therebetween.

Without being bound by any particular theory, it has been observed by the present inventors that when the above-described mol ratio is higher than 75:25 or lower than 25:75, the electrode is not sufficiently stable and/or its sensing efficiency is reduced.

In some of any of the embodiments described herein, the metal species, or the functional moiety comprising same, further comprises an oxide of the metal.

In some of any of the embodiments described herein, the metal species or the functional moiety comprising same comprises elemental metal (e.g., as metal particles), metal ions and metal oxides of a metal that promotes decomposition of peroxides, as described herein.

Without being bound by any particular theory, it is assumed that metal oxides can be generated on the electrode's surface when the metal particles or the metal ions contact oxygen present in the environment (e.g., in air or in the electrolyte). The formed metal oxides can also generate metal particles and/or metal ions upon application of potential.

In some of any of the embodiments described herein, an amount of the metal oxide is no more than 20 mol %, preferably no more than 15 mol %, or no more than 13 mol %, or no more than 12 mol %, or no more than 10 mol %, of the total amount of the metal species in the functional moiety (e.g., the total number of moles of the metal ions, metal particles and metal oxides in the functional moiety).

In some of any of the embodiments described herein, an amount of the metal oxide ranges from 1 mol % to 20 mol %, of the total amount of the metal species (e.g., the metal ions, particles and oxides in the functional moiety), including any intermediate values and subranges therebetween.

The metal oxide can be a mono-oxide (e.g., MO or $M_2O$), a di-oxide (e.g., $MO_2$ or $M_3O_2$), a tri-oxide (e.g., $MO_3$ or $M_2O_3$), and so forth, depending on the valency of the metal.

Similarly, a metal ion can be monovalent (M⁺), divalent (M⁺), trivalent (M⁺), and so forth, depending on the valency of the metal and on the counter ion.

M represents a metal, e.g., a metal as described herein.

It is to be noted that according to some of any of the embodiments described herein, metal oxides and metal ions (e.g., which form a part of a metal salt) are not to be seen as equivalents.

In some of any of the embodiments described herein, the metal oxide is in a form of particles, including microparticles, nanoparticles and a combination thereof.

In some of any of the embodiments described herein, a total amount of metal species in a form of particles (e.g., of elemental metal particles or of metal particles and metal oxide particles) ranges from 20 mol % to 70 mol %, of the total number of moles of the metal species (e.g., the metal ions, particles and oxides), including any intermediate values and subranges therebetween.

In some of any of the embodiments described herein, the metal species or the functional moiety comprising same comprises particles of both elemental metal and metal oxides and ions of a metal, and in some of these embodiments, a mol ratio of the metal ions and the total amount metallic particles (of elemental metal and of metal oxide) ranges from 75:25 to 25:75, including any intermediate values and subranges therebetween, and can be, for example, 75:25, 72:28, 70:30, 68:32, 65:35, 62:38, 60:40, 58:42, 55:45, 52:48, 50:50, 48:52, 45:55, 42:58, 40:60 38:62, 35:65, 32:68, 30:70, 28:72 or 25:75, including any intermediate values and subranges therebetween.

In some of any of the embodiments described herein, the metal species or the functional moiety comprising same comprises particles of both elemental metal and metal oxides and ions of a metal, and in some of these embodiments, a mol ratio of the metal ions and the elemental metal is as described herein in any of the respective embodiments, and a mol ratio of the elemental metal and the metal oxide ranges from 98:2 to 50:50, or from 96:4 to 60:40, including any intermediate values and subranges therebetween, and can be, for example, 98:2, 96:4, 95:5, 90:10, 85:15, 80:20, 75:25, 70:30, 68:32, 67:33, 66:34, 65:35, 64:36, 63:37, 62:38, 60:40, 55:45 or 50:50, including any intermediate values and subranges therebetween.

In some of any of the embodiments described herein, the metal species or the functional moiety comprising same comprises particles of both elemental metal and metal oxides and ions of a metal, and in some of these embodiments, a mol ratio of the metal ions and the elemental metal is as described herein in any of the respective embodiments, and a mol ratio of the metal ions and the metal oxide ranges from 10:1 to 4:1, or from 90:10 to 80:20, including any intermediate values and subranges therebetween, and can be, for example, 90:10, 88:12, 85:15, 82:18, or 80:20, including any intermediate values and subranges therebetween.

In some of any of the embodiments described herein, the metal species or the functional moiety comprising same comprises particles of both elemental metal and metal oxides and ions of a metal, and in some of these embodiments the functional moiety or the metal species comprises:

Metal ions, in an amount that ranges from 20 mol % to 80 mol %, or from 30 mol % to 70 mol %, including any intermediate value and subranges therebetween, of the total number of moles of the metal atoms in the functional moiety or metal species;

Elemental metal (e.g., as metal particles), in an amount that ranges from 10 mol % to 70 mol %, or from 20 mol % to 65 mol %, including any intermediate value and subranges therebetween, of the total number of moles of the metal atoms in the functional moiety or metal species; and Metal oxide (e.g., as particles) in an amount that ranges from 1 mol % to 30 mol %, or from 2 mol % to 15 mol %, including any intermediate value and subranges therebetween, of the total number of moles of the metal atoms in the functional moiety or metal species.

In some of any of the embodiments described herein, the metal species or the functional moiety comprising same comprises particles of both elemental metal and metal oxides and ions of a metal, and in some of these embodiments the functional moiety or the metal species comprises:

Metal ions, in an amount that ranges from 30 mol % to 70 mol %, or from 32 mol % to 62 mol %, including any intermediate value and subranges therebetween, of the total number of moles of the metal atoms in the functional moiety or metal species;

Elemental metal (e.g., as metal particles), in an amount that ranges from 25 mol % to 65 mol %, including any intermediate value and subranges therebetween, of the total number of moles of the metal atoms in the functional moiety or metal species; and Metal oxide (e.g., as particles) in an amount that ranges from 2.5 mol % to 12.5 mol %, including any intermediate value and subranges therebetween, of the total number of moles of the metal atoms in the functional moiety or metal species.

In some of any of these embodiments, the mol ratio between any two of these metal species is as described herein in any of the respective embodiments.

In some of any of the embodiments described herein, the metal particles are metal nanoparticles, having an average size (e.g., diameter) at a nanoscale range, as defined herein.

In some embodiments, an average size of the particles ranges from 1 nanometer to about 500 nanometers, or from 1 to 200 nanometers, of from 1 to 100 nanometers, including any intermediate values and subranges therebetween. In exemplary embodiments, the average size of the metal particles is about 40 nanometers.

In some of any of the embodiments described herein, the metal is silver, and the functional moiety comprises silver ions, optionally in combination with silver particles (e.g., silver nanoparticles as described herein) and/or silver oxide.

In some of any of the embodiments described herein, the functional moiety comprises an organic moiety that is associated with one or more of the metal species.

By "associated with" in the context of these embodiments it is meant that the organic moiety and the metal species are associated with one another by physical and/or, preferably, chemical (e.g., covalent, electrostatic, organometallic) interactions.

The organic moiety can be, for example, an organic anion that forms an organic salt with metal ions; or an organometallic ligand that forms with the metal or a metal oxide or a metal ion an organometallic complex.

In some of any of the embodiments described herein, the functional moiety is or comprises an organic salt of the metal, which comprises the metal ions (metal cations) and an organic anion.

Without being bound by any particular theory, it is assumed that the organic anion facilitates the attachment of the metal species to the electrode's surface, and thereby facilitates the attachment of the metal species (e.g., the metal ions and the generated metal particles and/or metal oxide) to the electrode's surface.

Exemplary organic anions include conjugate bases of organic acids such as, but not limited to, benzoic acid (benzoate), p-phenyl benzoic acid (p-phenyl benzoate), p-toluene sulfonic acid (p-toluene sulfonate), salicylic acid (salicylate), phenyl acetic acid (phenyl acetate), acetic acid (acetate), trifluoroacetic acid (trifluoroacetate), acetamidobenzoic acid (acetamido benzoate), phthalic acid (phthalate), terephthalic acid (therephthalate), propionic acid (propionate), butyric acid (butyrate), trifluoromethanesulfonic acid (trifluoromethanesulfonate), diethyldithiocarbamic acid (diethyldithiocarbamate), acetyl acetonic acid (acetylacetonate), methane sulfonic acid (methanesulfonate), cycloheane butyric acid (cyclohexanebutyrate), p-toluenesulfonic acid (p-toluenesulfonate), pentafluoropropionic acid (pentafluoropropionate), phthalocyanic acid (phthalocyanate), citric acid (citrate), hexafluoroacetylacetonic acid (hexafluoroacetylacetonate), 2,2-Dimethyl-6,6,7,7,8,8,8-heptafluoro-3,5-octanedionic acid (2,2-Dimethyl-6,6,7,7,8,8,8-heptafluoro-3,5-octanedionate), sulfadiazine, heptafluorobutyric acid (heptafluorobutyrate), tetrakis(acetonitrile) tetrafluoroboric acid (tetrakis(acetonitrile) tetrafluoroborate), cyanic acid (cyanate), thiocyanic acid (thiocyanate), and fatty acids such as stearic acid (stearate), oleic acid (oleate), lauric acid (laurate), lactic acid (lactate) and more.

In some of any of the embodiments described herein, the metal is silver and the functional moiety is or comprises an organic salt of silver, for example, silver benzoate.

In some embodiments, the functional moiety is attached to the electrode's surface by means of physical adsorption, such that, for example, the metal ions are adsorbed to and/or embedded in the microfibers forming the electrode.

In some of any of the embodiments described herein, the CF electrode further comprises an ion-permeable material attached to at least a portion of its surface.

In some embodiments, the ion-permeable material is a proton exchange membrane which is permeable to cations but do not conduct anions or electrons.

Any available proton exchange membrane can be used in the context of these embodiments of the invention, including, as non-limiting examples, carbon-based membranes and nickel-based membranes.

In some embodiments, the ion permeable material is a Nafion membrane, preferably a Nafion® Bilayer membrane such as, for example, Nafion® 112, Nafion® 115, Nafion® 117 and Nafion® 119, and any membrane in Nafion® series 900-2000. Any other ion-permeable material is contemplated.

In some embodiments, the ion-permeable material comprises, or is in a form of, a polymeric film, which is deposited onto the electrode's surface (or a portion thereof).

In some embodiments, the film is a thin film, featuring a thickness of from about 2 nm to about 200 µm, including any intermediate values and subranges therebetween.

In some embodiments, the ion permeable material (e.g., is a form of a polymeric film) is deposited on the same portion of the electrode's surface at which the metal ions and/or particles and/or oxides are deposited.

In some embodiments, the ion-permeable material serves to facilitate the physical attachment of the functional moiety (the metal species such as metal ions and metal particles and/or oxides) to the electrode.

In some embodiments, the functional moiety comprising the metal species (e.g., metal ions) and the ion-permeable material are selected such that the functional moiety physically interacts with the ion-permeable material.

Herein, "physical attachment", "physical interaction" and grammatical diversions thereof describe interactions which do not involve chemical covalent or electrostatic bonds, and include interactions such as absorption (possibly via hydrogen bonds and/or hydrophobic interactions), entrapment, entanglement, incorporation, coating or any other interaction that leads to interconnection between the indicated substances.

Without being bound by any particular theory, the functional moiety and the ion-permeable material are selected such that the functional moiety (e.g., the metal species) does no penetrate membrane pores of the ion-permeable material, and thus remains attached to the electrode.

A sensing electrode as described herein in any of the respective embodiments, is also referred to interchangeably as a modified CF electrode, or a modified CF microelectrode, or silver-modified CF electrode, or silver-modified CF microelectrode and diversions and variations thereof.

Sensing System:

In some of any of the embodiments described herein, the sensing electrode as described herein is usable for electrochemical detection of a peroxide-containing compound in a sample.

In some of any of the embodiments described herein, the sensing electrode as described herein is usable for electrochemically determining a presence and/or level of a peroxide-containing compound in a sample.

In some of any of the embodiments described herein, the sensing electrode as described herein is usable for determining a presence and/or level of a peroxide-containing compound in a sample, upon integrating the electrode in an electrochemical cell.

In some embodiments of the present invention, there is provided an electrochemical cell which comprises a sensing electrode as described herein in any of the respective embodiments and any combination thereof. The sensing electrode functions as a working electrode.

In some embodiments of the present invention, there is provided a sensing system which comprises a sensing electrode as described herein in any of the respective embodiments and any combination thereof. Such a sensing system is also referred to as a sensor.

In some embodiments of the present invention, there is provided a sensing system which comprises an electrochemical cell as described herein in any of the respective embodiments and any combination thereof.

The following describes some embodiments of an electrochemical cell of the invention.

In some of any of the embodiments described herein, the sensing electrode is electrically connectable to a power source, and the cell is configured such that when it is operated, at least a portion of the sensing electrode, i.e., a portion thereof that have functional moieties as described herein deposited on the electrode's surface), contacts the analyte (a peroxide-containing compound or a sample containing same).

In some embodiments of the present invention, the electrochemical cell further comprises a reference electrode. Any commercially available or customarily designed reference electrode is contemplated.

In some of any of the embodiments described herein, the reference electrode is an aqueous reference electrode. Exemplary usable reference electrodes include, but are not limited to, Silver/Silver Chloride electrode (e.g., Ag/AgCl/Saturated KCl electrode such as marketed by Metrohm), a Standard calomel (e.g., saturated calomel) electrode (SCE), a Standard hydrogen electrode (SHE), a Normal hydrogen electrode (NHE), a Reversible hydrogen electrode (RHE), a Copper-copper(II) sulfate electrode (CSE); a pH-electrode;

a Palladium-hydrogen electrode, a Dynamic hydrogen electrode (DHE), and a Mercury-mercurous sulfate electrode (MSE).

The reference electrode is also electrically connectable to a power source, and the cell is configured such that when it is operated, a potential difference (voltage) is applied between the sensing electrode and the reference electrode.

In some embodiments, the electrochemical cell follows a three-electrode design and further comprises an auxiliary electrode. Preferably, but not obligatory, the auxiliary electrode is also a carbon electrode, preferably a glassy carbon electrode. Any other auxiliary electrode, commercially available or customarily designed, is contemplated. Non-limiting examples include gold electrodes, other carbon electrodes, platinum electrodes and carbon/gold electrodes.

In some embodiments, the auxiliary electrode is electrically connectable to the sensing electrode.

In some of any of the embodiments described herein, the electrochemical cell further comprises a device that measures a current generated at the sensing electrode, as a result of redox reactions occurring at or next to a surface of the sensing electrode. In some embodiments, this device (e.g., an amperometer, a picoameter) is electrically connectable to the auxiliary electrode and the sensing electrode.

A schematic presentation of an exemplary assembly of a three-electrode electrochemical cell 10 according to some embodiments of the present invention is presented in FIG. 6.

Electrochemical cell 10 comprises a sensing electrode 12 as described herein, which acts as a working electrode. Sensing electrode 12 features functional moieties 16 as described herein (e.g., metal ions such as silver ions as described herein, optionally in combination with metal particles and/or metal oxides, as described herein, and optionally an ion-permeable material as described herein) at least on a portion of a surface thereof. When the cell is operated, the portion of the electrode that features functionalized moieties 16 should be in contact with the analyte, e.g., by contacting an electrolyte 18 in which the analyte is dissolved. Sensing electrode 12 is one half of electrochemical cell 10. A reference electrode 22 is the other half of cell 10. A power source 20 is electrically connectable to sensing electrode 12 and reference electrode 22 by means of electrical wires 24. Power source 20 is configured to apply voltage between sensing electrode 12 and reference electrode 22, for example, by applying potential to one of the electrodes. Optionally, but not obligatory, cell 10 further comprises an auxiliary electrode 26, and a current measuring device 28, and device 28 is electrically connectable to sensing electrode 12 and auxiliary electrode 26.

For an electrochemical cell (e.g., cell 10) to operate, at least the sensing electrode (electrode 12) should be in contact with an electrolyte solution shown in FIG. 6 as an electrolyte solution 18. The electrochemical cell (e.g., cell 10) can comprise an electrolyte solution (e.g., electrolyte solution 18, as exemplified in FIG. 6), or can comprise means (e.g., an inlet port; not shown in FIG. 6), for introducing the electrolyte to the cell, so as to contact at least the sensing electrode (e.g., sensing electrode 12).

An electrochemical cell according to the present embodiments can follow any of the designs known in the art, and can include one or more sensing electrodes, and one or more of a reference electrode and/or an auxiliary electrode. Exemplary designs include, without limitation, rotating disk-ring electrodes, ultramicro-electrodes, or screen printed electrodes.

The configuration of the components of electrochemical cell 10 as presented in FIG. 6 are for illustrative purpose only and are not to be regarded as limiting in any way.

Electrochemical cell 10 can be, for example, in a form of a covered glass (or other inert material like Teflon or quartz) beaker, containing the sample solution in which the three electrodes are dipped. In some embodiments, electrochemical cell 10 is a micro cell or a thin layer cell.

Electrochemical cell 10 may further comprise means for mixing/stirring a sample with electrolyte 18 (not shown in FIG. 6).

Electrochemical cell 10 may further comprise means for monitoring and/or controlling the temperature inside the cell (not shown in FIG. 6).

As used herein and in the art, an electrolyte is an electrically conducting material or medium. An electrolyte can be solid or fluid, and can be used per se or when dissolved in a polar solvent, such as water. When dissolved is a solvent, it is referred to as an electrolyte solution. In the context of electrochemical cells, an electrolyte is also referred to as a background solution.

Herein throughout, the term "electrolyte" also encompasses an "electrolyte solution", unless specifically indicated otherwise.

In an electrochemical cell as described herein (e.g., cell 10, FIG. 6), at least the sensing electrode (e.g., sensing electrode 12) contacts the electrolyte solution (e.g., electrolyte solution 18) when the cell is operated. In some embodiments, all electrodes contact an electrolyte solution (e.g., electrolyte solution 18) when the cell is operated. In some embodiments, all electrodes contact the same electrolyte solution, as exemplified in FIG. 6, and in some embodiments, one or more of the electrodes contact an electrolyte solution different from the electrolyte solution in contact with the sensing electrode, and a membrane is interposed between the different electrolyte solutions.

In some of any of the embodiments described herein, the electrolyte solution (e.g., electrolyte solution 18, FIG. 6), features an alkaline pH, that is, a pH higher than 7, or higher than 7.4, or higher than 8, or higher than 10, or higher than 11, for example, pH 12, or higher.

In some of any of the embodiments described herein, the electrolyte solution (e.g., electrolyte solution 18, FIG. 6), features a pH in a range of from 8 to 14, or from 8 to 13, or from 8 to 12, or from 10 to 14, or from 10 to 13, or from 10 to 12.

In some of any of the embodiments described herein, the electrolyte solution (e.g., electrolyte solution 18, FIG. 6) is or comprises an aqueous solution, e.g., an alkaline aqueous solution, featuring a pH as described herein.

In some of any of the embodiments described herein, the electrolyte solution (e.g., electrolyte solution 18, FIG. 6) comprises a mixture of an aqueous solution and an organic solvent.

Exemplary alkaline aqueous solutions include aqueous solutions of water soluble alkaline substances, for example, metal alkali hydroxides such as sodium hydroxide, potassium hydroxide, or of metal-earth hydroxides, such as magnesium hydroxide or calcium hydroxide. Exemplary alkaline aqueous solutions include also a buffer solution that provides the desired pH value, as described herein. Buffer solutions that provide an alkaline pH as described herein are well known to those skilled in the art.

Exemplary organic solvents include water-miscible solvents, preferably polar and/or aprotic solvents, and, further preferably, in which the peroxide-containing solvent is dissolvable and/or in which an organic quaternary ammonium salt of choice, as described herein, is dissolvable.

Suitable organic solvents are preferably further characterized as capable of inhibiting or reducing electrolysis of water and/or of broadening the electrochemical window of water, for example, up to −2 Volts.

Suitable organic solvents are preferably further characterized as being chemically compatible with (e.g., chemically inert to) the electrochemical cell or system as described herein. In some embodiments, the organic solvent is characterized as being chemically compatible with plastic and/or any other polymeric or glassy materials typically used for constructing electrochemical cells or systems.

An exemplary solvent is acetonitrile, although other solvents, such as, for example, dimethyl formamide, dimethylsulfoxide, propylene carbonate, ethanol, methanol, N-methylpyrrolidone, tetrahydrofuran, ethyl acetate, acetone, dimethyl ether, pyridine, diethyl ether, hexamethylphosphoric triamide, and hexamethylphosphorous, and any mixture thereof, are contemplated. Another exemplary solvent is ethanol.

A volume ratio between an aqueous solution and an organic solvent can range, for example, from 10:1 to 1:1, or from 5:1 to 1:1, or from 3:1 to 1:1, or from 5:1 to 3:1, including any intermediate value and subranges therebetween. For example, an electrolyte solution can comprise 90 vol. % aqueous solution and 10 vol. % organic solvent, or 80 vol. % aqueous solution and 20 vol. % organic solvent, 75 vol. % aqueous solution and 25 vol. % organic solvent, or 70 vol. % aqueous solution and 30 vol. % organic solvent, or 65 vol. % aqueous solution and 35 vol. % organic solvent, or 60 vol. % aqueous solution and 60 vol. % organic solvent, or 55 vol. % aqueous solution and 45 vol. % organic solvent, or 50 vol. % aqueous solution and 50 vol. % organic solvent. In some embodiments, an electrolyte solution comprises 70 vol. % aqueous solution and 30 vol. % organic solvent.

In some of any of the embodiments described herein, an electrolyte solution (e.g., electrolyte solution 18, FIG. 6), comprises a soluble salt (e.g., a water-soluble salt, or a salt soluble in the solvent mixture making up the electrolyte solution). Any soluble salt commonly used in electrolyte solution for increasing the ionic strength is contemplated, typically an inorganic salt, with potassium chloride being a non-limiting exemplary salt. A concentration of the salt typically determines, at least in part, the ionic strength of the electrolyte solution and can range from, for example, 0.1M to 1M, or from 0.1M to 0.5M, including any intermediate value and subranges therebetween. In some embodiments, a concentration of the salt is 0.25M.

In some of any of the embodiments described herein, the electrolyte solution comprises a quaternary ammonium salt, preferably, an organic quaternary ammonium salt. An organic quaternary ammonium salt can be represented by the Formula:

$R_1R_2R_3R_4N^+X^-$ wherein: $R_1$, $R_2$, $R_3$ and $R_4$ is each independently an alkyl, cycloalkyl or aryl, or alternatively, two or more form together a heterocylic (heteroalicyclic or heteroaryl) ring; and X is an anion such as halide, (e.g., chloride, bormide, iodide), perchlorate, borate, and any other acceptable anion.

The selection of the anion can be made such that it is inert to the electrochemical window of water, that is, the anion is preferably such that features a standard electrode potential higher than hydroxide.

In some embodiments, the anion is other than halide.

In some embodiments, $R_1$, $R_2$, $R_3$ and $R_4$ is each independently an alkyl, and in some embodiments, each is independently an alkyl of from 1 to 4 carbon atoms.

In some of any of the embodiments described herein, the organic quaternary ammonium salt is soluble in the electrolyte solution as described herein in any of the respective embodiments.

Exemplary organic quaternary ammonium salts that are usable in the context of the present embodiments include commonly used phase transfer catalysts.

In some of any of the embodiments described herein, a concentration of the quaternary ammonium salt is lower than 0.5 M, or lower than 0.2M, or lower than 0.1 M. In some embodiments, a concentration of the quaternary ammonium salt ranges from 1 to 10 mM, including any intermediate values and subranges therebetween. In some embodiments, a concentration of the quaternary ammonium salt is 5 nM.

In some of any of the embodiments described herein, the quaternary ammonium salt is such that assists in providing a sharp peak of the oxygen reduction and/or of the peroxide reduction.

Non-limiting examples of a quaternary ammonium salt include tetrabutylammonium iodide and tetrabutylammonium perchlorate, although other quaternary ammonium compounds are contemplated.

An exemplary electrolyte solution according to the present embodiments in described in the Examples section that follows. As exemplified therein, an electrolyte solution comprising a mixture of an aqueous NaOH solution, having pH 12, an organic solvent, and an organic quaternary ammonium salt at a low concentration, when used in combination with a sensing electrode as described herein, enables to separate the reduction peaks generated in the presence dissolved oxygen and also of hydrogen peroxide and allows performing electrochemical detection while circumventing the need to deaearate (e.g., evacuate oxygen from) the cell or system, and while overcoming faults caused by interference of traces of hydrogen peroxide that are typically present in peroxide-containing compounds.

In some of any of the embodiments described herein, an electrochemical cell and/or a sensing system comprising same, as described herein, is operable when a concentration of oxygen in the electrolyte is at least 1 ppm, or at least 10 ppm, or at least 20 ppm, or at least 30 ppm, or higher.

In some of any of the embodiments described herein, electrochemical detection of a peroxide-containing compound is performed using an electrochemical cell and/or a sensing system comprising same, as described herein, when a concentration of oxygen in the electrolyte is at least 1 ppm, or at least 10 ppm, or at least 20 ppm, or at least 30 ppm, or higher.

In some of any of the embodiments described herein, an electrochemical cell and/or a sensing system comprising same, as described herein, is operable when a concentration of oxygen in the electrolyte is higher than a concentration of a peroxide-containing compound in the electrolyte by at least 10-folds, or at least 20 folds, or at least 30-folds, or at least 50-folds or at least 100-folds, or at least 1000-folds or at least 5000-folds, and even higher.

In some of any of the embodiments described herein, electrochemical detection of a peroxide-containing compound is performed using an electrochemical cell and/or a sensing system comprising same, as described herein, when a concentration of oxygen in the electrolyte is higher than a concentration of a peroxide-containing compound in the electrolyte by at least 10-folds, or at least 20 folds, or at least 30-folds, or at least 50-folds or at least 100-folds, or at least 1000-folds or at least 5000-folds, and even higher.

In some of any of the embodiments described herein, the sensing system and/or the electrochemical cell described herein is/are devoid of means for deaerating the system or cell prior to contacting the sensing electrode with a sample. Such means typically include physical means for introducing an inert gas, such as argon gas or nitrogen gas, to the cell, and optionally a source of the inert gas connectable to the means; and/or means for chemically removing oxygen, for example, zinc or sodium sulfate.

In some of any of the embodiments described herein, the sensing system and/or the electrochemical cell described herein is/are devoid of means for bubbling an inert gas in the electrolyte solution and/or means for connecting the cell and/or the system to a source of an inert gas.

In some of any of the embodiments described herein, the sensing system and/or the electrochemical cell described herein is/are devoid of zinc, sodium sulfate, or any other chemical reagents that can react with oxygen; and/or is/are devoid of means of contacting oxygen with such chemical reagents.

In some of any of the embodiments described herein, a system as described herein further comprises means for introducing a sample to the electrochemical cell. The sample should be introduced to the cell such that it contacts the sensing electrode.

In some embodiments, the sensing system comprises means for introducing a sample to the electrochemical cell such that it contacts the sensing electrode.

In some embodiments, the sensing system comprises means for introducing a sample to the electrochemical cell such that it is mixed with or dissolved in the electrolyte solution.

In some embodiments, a sample is introduced to the electrochemical cell by means of an inlet port, referred to herein also as a sample inlet. In some embodiments, the inlet port is configured for introducing a gaseous sample to the cell. In some embodiments, the inlet port is configured for introducing a liquid sample to the cell. In some embodiments, a fluid (gaseous and/or liquid) sample is bubbled into the electrolyte solution and the inlet port is configured for effecting such bubbling.

In some of any of the embodiments described herein, the system is devoid of a sample inlet. This is enabled by the carbon fiber electrode, which is gas permeable and hence gas samples can enter the electrochemical cell therethrough.

In some of any of the embodiments described herein, the means for introducing a sample to the electrochemical cell include a pump or a pumping device. An exemplary pump is an air pump, in cases where the sample is in a gaseous form. The pump or the pumping device can be in contact with the CF microelectrode of the present embodiments, such that the pumped sample permeates through the electrode and is thus introduced to the cell or system. Alternatively, the pump or pumping device are in contact with the electrolyte, such that the pumped sample contacts or is mixed with the electrolyte.

In some of any of the embodiments described herein, a system as described herein further comprises a gas outlet.

In some of any of the embodiments described herein, a sensing system as described herein is operable by assembling at least a sensing electrode as described herein and an electrolyte solution, and electric means for electrically connecting the sensing electrode to a power source; introducing a sample into the electrochemical cell, by means that allow the sample to contact (e.g., dissolve in) the electrolyte solution, as described herein; electrically connecting the sensing electrode to the power source; applying a potential to the sensing electrode, by means of a power source as described herein; and measuring an electrochemical signal that is indicative of an electrochemical reaction in which the peroxide-containing compound participates.

In some of any of the embodiments described herein, the electrochemical signal is an electrical current generated at the sensing electrode is response to said potential, and measuring the signal is effected by means of an electrical current measuring device. The measured current is indicative of a presence and/or level (e.g., amount, concentration) of a peroxide-containing compound in the sample.

In some of any of the embodiments described herein, the electrochemical cell comprises a reference electrode and applying a potential is effected by applying voltage between the sensing electrode and the reference electrode.

In some of any of the embodiments described herein, the power source is configured to apply potential to the sensing electrode according to any known voltammetry method, as described in further detail hereinafter, in embodiments related to a sensing method.

In some embodiments, the power source is configured to apply a varying potential to the sensing electrode, and in some embodiments, the power source is configured to apply a linearly varying potential (as in linear sweep voltammetry); a staircase varying potential; a squarewave varying potential; or a pulse varying potential (normal pulse or differential pulse), as described in further detail hereinbelow.

In some embodiments, the power source is configured to apply a varying potential to the sensing electrode in a linear sweep mode.

In some of any of the embodiments described herein, the system is configured such that the functional moiety comprises metal ions and metal particles and/or metal oxides, as described herein in any of the respective embodiments.

In some of any of the embodiments described herein, the system is configured such that upon potential application, a portion (e.g., less than 70 mol %, or less than 60 mol %, or less than 50 mol) of total amount of the metal species initially deposited on the electrode's surface (e.g., metal ions) is converted to metal particles.

In some of any of the embodiments described herein, the functional moiety comprises metal ions and the system is configured such that upon application of a potential, a portion of the metal ions, as described herein, is converted into metal particles.

In some of any of the embodiments described herein, the system is configured such that upon potential application, the functional moiety comprises metal particles in an amount that ranges from 20 mol % to 70 mol % of the total number of moles of metal species in the functional moiety, as described herein in any of the respective embodiments.

In some of any of the embodiments described herein, the system is configured such that the functional moiety comprises particles of a metal and ions of the same metal, and a mol ratio of the ions of the metal and the particles of the metal ranges from 75:25 to 25:75 or from 70:30 to 30:70, as described herein in any of the respective embodiments.

In some of any of the embodiments described herein, system is configured such that upon potential application, the functional moiety comprises particles of a metal and ions of the same metal, and oxide of the same metal, and a mol ratio of the ions of the metal and the particles of the metal, or of the ions of the metal and the total amount of metal particles (e.g., particles of elemental metal and of the metal oxide), or of the metal ions and the metal oxide or of the elemental metal and the metal oxide are as described herein in any of the respective embodiments.

In some of any of the embodiments described herein, the system is configured such that upon potential application, the functional moiety comprises particles of a metal and ions of the same metal, and oxide of the same metal, each in an amount as described herein in any of the respective embodiments.

In some of any of the embodiments described herein, the system is configured to determine a current generated in response to the varying potential, and in some embodiments, the system is configured for determining a change in the current generated at the sensing electrode, in response to the varying potential.

In some of any of the embodiments described herein, the system is configured to determine an electric current or a change in an electric current, compared to an electric current or a change in the electric current generated at the sensing electrode, in response to the varying potential, when a sample is not introduced to the electrochemical cell. Such data is also referred to herein as "background current, and in some embodiments, the system is configured to subtract the background current from the determined current or change in current.

In some embodiments, the system is operable in a linear sweep voltammetry mode and is configured to determine a change in an electrical current in response to a linear change in the potential, as is known in the art.

Generally, but not necessarily, the system is configured for providing a voltammogram that presents values that are in line with the voltammetry methodology used.

Determination of an electrical current, or a change in an electrical current, according to any of the respective embodiments, can be performed by means of a device which is configured to process the received signals (e.g., the mode of the applied varying potential and corresponding generated current data) so as to provide a value or a set of values as desired (e.g., a change in electrical current relative to the applied potential, or any other voltammogram). Such a device is also referred to herein as a signal processor.

In some of any of the embodiments described herein, the signal processor is a data processor such as a computer configured for receiving and analyzing the signals. The signal processor extracts, from each generated signal or set of signals, a parameter (e.g., a voltammogram) that is indicative of an electrochemical reaction of a peroxide-containing compound, and hence of a presence and/or level of the peroxide-containing compound.

In some embodiments of the invention the signal processor is configured to construct a fingerprint of a peroxide-containing compound, for example, a voltammogram obtained upon contacting an electrolyte solution with the peroxide-containing compound and applying a certain mode of a varying potential (e.g., a linear sweep potential).

In some embodiments of the invention the signal processor is configured to construct a database of fingerprints of a plurality of peroxide-containing compounds, for example, a database of voltammograms obtained upon contacting an electrolyte with a peroxide-containing compound and applying a certain mode of a varying potential (e.g., a linear sweep potential). The database can include several voltammograms for each peroxide-containing compound, each for a different mode and/or range and/or rate of application of the varying potential, and/or each for a different electrolyte.

In some embodiments of the invention the signal processor is configured to search a database of fingerprints of a plurality of peroxide-containing compounds, for example, a database of voltammograms as described herein, for a fingerprint that matches a received fingerprint, and to identify accordingly the peroxide-containing compound.

In some of any of the embodiments of the invention the signal processor is configured to determine a level of an identified peroxide-containing compound in a sample, by accessing and/or processing relevant data. Such data can include, for example, a calibration curve, e.g., of voltgammograms, or of specific values obtained in voltammetry measurements (e.g., a reduction peak), obtained for varying concentrations of the identified peroxide-containing compound, and stored on a computer readable medium. For example, the signal processor may access the calibration curve, search for a value (e.g., a reduction peak) that matches the value obtained upon operating the system, and identify a concentration of the identified peroxide-containing compound that matches this value. Alternatively, or in addition, the data include a lookup table stored on a computer readable medium, which can be searched for values that match the measured value and are indicative of a level of an identified peroxide-containing compound. Further alternatively, or in addition, the data include a predetermined relationship between the measured value and a level of the identified peroxide-containing compound. For example, if such a predetermined relationship comprises a linear relationship, the signal processor can determine the level of an identified peroxide-containing compound by means of extrapolation, based on the pre-determined relationship.

In some of any of the embodiments described herein, the sensing system as described herein further comprises an additional sensing electrode, which is configured to generate an electrical signal upon contacting a compound other than a peroxide-containing compound. In some of these embodiments, the additional sensing electrode forms a part of an additional electrochemical cell. Such a system is configured such that a sample is introduced therein and contacts both sensing electrodes. The generated electrical signals are thus indicative of the presence/absence and amount (if present) of both the peroxide-containing compound and the other compound.

In some embodiments, such a sensing system further comprises a signal processor as described herein which is configured to identify the peroxide-containing compound, as described herein, and to identify the other compound, and, optionally, to further determine a level of each identified compound in a sample.

In some embodiments, the additional sensing electrode is a carbon electrode which is modified so as to detect the additional compound.

In some embodiments, the additional sensing electrode is configured to detect explosives other than peroxide-containing explosives, for example, nitro-containing compounds.

In some of any of the embodiments described herein, a sensing system as described herein comprises a plurality (e.g., two, three or more) of modified CF microelectrodes as described herein, wherein at least one portion of the CF microelectrodes is modified so as to feature a first functional moiety and at least another portion of the CF microelectrodes features a second functional moiety which is different from the first functional moiety, whereby both functional moieties interact with a peroxide-containing material as described herein in any of the respective embodiments.

In some of these embodiments the sensing system comprises three, four or more portions of CF microelectrodes, each featuring a different functional moiety that interacts with a peroxide-containing compound as described herein.

In some of any of these embodiments, the sensing system comprises a plurality of electrochemical cells or a plurality of electrochemical half cells, each being individually connectable to a power source, and, optionally, each being individually connectable to a device for measuring the electrochemical parameter as described herein.

In some of any of these embodiments, each of the measuring devices can independently be connected to a signal processor, or, alternatively, all measuring devices are connected to the same signal processor.

Such a sensing system can generate for different peroxide-containing compounds different defined fingerprints, and allows using, for example, a dedicated database, for the identification of the peroxide-containing compound based on such fingerprints database, according to the guidelines provided herein.

Electrochemical Detection:

According to an aspect of some embodiments of the present invention there is provided a method of detecting a peroxide-containing compound in a sample, while utilizing a sensing electrode as described herein in any of the respective embodiments.

In some embodiments, a method as described herein utilizes a sensing electrode and an electrolyte solution, as described herein in any of the respective embodiments.

In some embodiments, a method as described herein utilizes a sensing system, as described herein in any of the respective embodiments.

In some embodiments, a method as described herein is devoid of a step of deaerating the electrolyte or a cell or a system comprising the electrolyte prior to performing the detection.

In some embodiments, a method as described herein is performed when a concentration of dissolved oxygen in the electrolyte at the time of detection is at least 1 ppm, and/or is higher by at least one order of magnitude than a concentration of the peroxide-containing compound in the electrolyte, as described herein.

Herein throughout, the terms "detection", "detecting" and grammatical diversions thereof, and the terms "sensing", are used interchangeably, and refer to determining a presence and/or level of a peroxide-containing compound.

In some of embodiments, the method as described herein is a method of electrochemical detection of peroxide-containing compounds.

In some embodiments, the method is effected by contacting a sensing electrode as described herein in any of the respective embodiments with a sample, and applying a potential to the sensing electrode.

In some embodiments, the method is further effected by measuring an electrochemical parameter upon applying the potential to the sensing electrode, and in some embodiments, the electrochemical parameter is an electrical current generated at the sensing electrode or a change in the electrical current at the sensing electrode. A presence and/or level of the electrochemical parameter is indicative of a presence and/or level of the peroxide-containing compound.

In some embodiments, the sensing electrode forms a part of an electrochemical cell as described herein in any of the respective embodiments, or a part of a sensing system as described herein in any of the respective parameters, and contacting the sensing electrode with the sample is effected by introducing the sample to the electrochemical cell or system, as described herein.

The sample can be introduced to the cell or system by means of a sample inlet, or by means of a pump, as described herein.

In some embodiments, contacting the sensing electrode with the sample is effected by introducing the sample to an electrolyte solution, preferably an electrolyte solution as described here in any of the respective embodiments.

In some embodiments, contacting the sensing electrode with the sample is effected by contacting a gas permeable sensing electrode with a gaseous sample for example, by means of an air pump as described herein.

In some embodiments, the electrolyte and the sensing electrode form a part of an electrochemical cell or sensing system as described herein, and in some of these embodiments, the sensing electrode contacts the electrolyte.

In some embodiments, the method further comprises contacting the sensing electrode with the electrolyte, either prior to or subsequent to introducing the sample to the electrolyte.

In some embodiments, applying a potential to the sensing electrode is performed immediately after contacting the sensing electrode with the sample.

In some embodiments, applying a potential to the sensing electrode is performed immediately after contacting the sensing electrode with the sample.

In some embodiments, applying a potential to the sensing electrode is performed immediately after contacting the sensing electrode with an electrolyte to which the sample was introduced.

In some embodiments, applying the potential is performed while a concentration of dissolved oxygen in the electrolyte is at least 1 ppm, as described herein.

In some embodiments, the sensing electrode forms a part of an electrochemical cell as described herein and applying the potential is performed by applying a voltage between the sensing electrode and a reference electrode.

In some embodiments the potential is a varying potential.

In some embodiments, measuring an electrochemical parameter is by a voltammetry experiment.

As known in the art, voltammetry experiments are conducted for obtaining information (e.g., presence, identity and/or level) of an analyte by measuring a generated current or a change in the current in response to application of a varying potential.

In order to obtain a quantitative measurement of an analyte (e.g., a peroxide-containing compound as described herein) by potentiostatic electrochemical analysis, the amount of electrons used for the reductive decomposition of the analyte should be monitored. In thermodynamic equilibrium the ratio of the redox-reactive species at the surface of the electrode can be obtained by Nernst equation:

$$E = E^0 + \frac{2.3RT}{nF} \log\left(\frac{C_O}{C_R}\right)$$

Where $C_O$ is the concentration of the oxidized form, and $C_R$ is the concentration of the reduced form, E is electrode potential, $E^0$ is standard electrode potential, R is the gas constant $$\left(8.314 \frac{J}{Kmol}\right),$$

T is the temperature (Kelvin scale), n is the number of electrons participate in the redox reaction and F is the Faraday constant (96,487 coulombs).

The entire measured current is composed of Faradic currents and non-Faradaic charging background current. The Faradic current obtained by the electrochemical reaction behaves according to Faraday's low, which means that 1 mole of redox active substance will involve a charge change of n×96,487 coulombs.

The information retrieved by voltammetry experiments, in its simplest form, is obtained as a voltammogram of I=f(E).

A voltammogram is a current versus potential curve used to describe the analyte's electrochemical reaction performed at the electrode as a result of the applied potential, and its derived current. It may have a complicated multi-stepped shape according to the complexity of the chemical reaction.

In some embodiments, and depending on the type of voltammetry used, the potential is varied continuously or stepwise or in pulses.

In some embodiments, the potential or varying potential applied to the sensing electrode is such that allows reductive decomposition of the peroxide-containing compound.

Exemplary potentials that can be applied to a sensing electrode as described herein range from 0 to about −2 Volts.

Voltammetry experiments can be categorized as linear sweep voltammetry and cyclic voltammetry.

Cyclic voltammetry is the process of electrochemical analysis in which the applied voltage is of a multi or mono-triangular shape. The resulting plot of current versus linear triangular potential scan of the working electrode is called cyclic voltammogram, while the plot of current versus linear potential scan of the working electrode is called linear sweep voltammogram. Cyclic voltammetry is usually the preliminary process used to determine the reduction potential of an analyte, the media's influence and the thermodynamics, as well as kinetics, of the electrochemical reaction.

In response to the triangular shaped potential, the measured current of the electrochemical cell that contained initially only the oxidized species, gradually increases up to a sharp peak at $E_{p[red]}$, followed by current decrease when most species adjacent to the electrode surface are reduced. When reversing the potential's direction, a gradual increase of current at the opposite direction ends in a sharp peak at $E_{p[ox]}$, where the chemical reaction proceeds to the opposite direction towards the oxidized form. When most species adjacent to the electrode surface are oxidized, the current decreases until the point of potential reverses, and so on.

Since an electrochemical reaction is located at the interface between the working electrode and the electrolyte solution, the reduced and oxidized species causing the sharp peaks of the voltammogram are concentrated to a narrow diffusive layer adjacent to the electrode. As a result, the shape of the curve's peak depends on the rate of diffusion. The peak's incline correlative to the concentration of electroactive particles on the electrode's surface, while the sharp decline depends solely on time, and results from the absence of electroactive particles near the surface due to limited diffusion.

In order to increase the sensitivity of voltammetric measurements, the share of the Faradic currents in the obtained voltammogram can be increased on the expense of the non-faradaic background current. Such alterations are enabled by applying a series of short duration potential steps (each last for several milliseconds) in a technique termed "pulse voltammetry". At the end of each potential step, two different current decay rates are obtained: sharp exponential decay to a negligible level is characteristic to the charging current, while slower decay is typical to the Faradic current. By recording the current's signal at the later regime, more of the signal is attributed to the Faradic current, while the contribution of the charging current is negligible. The differential pulse voltammogram is obtained from the subtraction of the pre-pulse current from the current that is obtained after the pulse is switched off, plotted against the applied potential. The corresponding sensitivity is thereby increased. The differential pulse voltammetry techniques vary by the shape of the applied potential waveform, and the current sampling technique.

Alongside increased sensitivity, differential pulse voltammetry allows the detection of two different analytes with similar redox potentials, by analysis of the peak's width according to the number of electrons that participate in their redox reaction. Exemplary values used for differential voltammetry measurements are 25-50 mV for current pulse amplitudes and 5 mV/second for the scan rate, while steeper amplitudes and faster scan rates are also contemplated.

In some of any of the embodiments described herein, the potential is a linearly varying potential.

In some of any of the embodiments described herein, the potential is a differential pulse varying potential.

In some of any of the embodiments described herein, the range of a varying potential ranges from −2 to +1 Volts, including any intermediate subranges therebetween.

In some of any of the embodiments described herein, an electrochemical parameter measured in a method as described herein is a change in electrical current relative to a derivative of the applied potential, although any other voltammogram is contemplated.

In some of any of the embodiments described herein, the measured electrochemical parameter is processed by a signal processor, as described herein in any of the respective embodiments, to thereby determine a presence, a composition and/or a level of one or more nitro-containing compounds in the sample.

In some of any of the embodiments described herein, a time ranging from introducing a sample so as to contact the sensing electrode to measuring the electrochemical parameter is less than 2 minutes, or less than 1 minute, or even less than 30 seconds, or less than 20 seconds, or less.

In some of any of the embodiments described herein, the method further comprises, prior to contacting the sample with the sensing electrode (e.g., prior to introducing the sample to the electrochemical cell), applying the potential, and measuring the electrochemical parameter, to thereby measure a background signal. In some embodiments, upon measuring the electrochemical parameter resulting from contacting the sensing system and the sample, the background signal is subtracted from the measured electrochemical parameter.

In some of any of the embodiments described herein, the method further comprises, prior to contacting the sample with the sensing electrode (e.g., prior to introducing the sample to the electrochemical cell), repetitively applying a potential, for at least 2 consecutive cycles. In some embodiments, the potential is applied from 2 to 20, or from 5 to 20, or from 5 to 15, or for 10, cycles, prior to contacting the sample with the sensing electrode.

In some embodiments, repetitively applying the potential is performed (the number of consecutive cycles is selected) prior to contacting the sample such that up to 70 mol %, or up to 65 mol % of the total number of moles of metal species is in a form of metal particles, as described herein in any of the respective embodiments.

In some embodiments, repetitively applying the potential is performed (the number of consecutive cycles is selected), prior to contacting the sample, such that up to 50 mol %, or up to 40 mol % of the total number of moles of metal species originally deposited on the electrode's surface (before applying the potential) is transformed (converted) to metal particles, as described herein in any of the respective embodiments.

In some embodiments, repetitively applying the potential is performed (the number of consecutive cycles is selected), prior to contacting the sample, such that the functional moiety comprises ions of a metal and particles of the same metal (in elemental form), and such that a mol ratio of the metal ions and the metal particles ranges from 75:25 to 25:75, or from 70:30 to 30:70, as described herein in any of the respective embodiments.

In some embodiments, repetitively applying the potential is performed (the number of consecutive cycles is selected), prior to contacting the sample, such that the functional moiety comprises particles of a metal and ions of the same metal, and oxide of the same metal, and a mol ratio of the ions of the metal and the particles of the metal, or of the ions of the metal and the total amount of metal particles (e.g., particles of elemental metal and of the metal oxide), or of the metal ions and the metal oxide or of the elemental metal and the metal oxide are as described herein in any of the respective embodiments.

In some embodiments, repetitively applying the potential is performed (the number of consecutive cycles is selected), prior to contacting the sample, such that the functional moiety comprises particles of a metal and ions of the same metal, and oxide of the same metal, each in an amount as described herein in any of the respective embodiments.

In some of any of the embodiments described herein, the method further comprises, subsequent to measuring the electrochemical parameter, applying an opposite potential to the sensing electrode, to thereby regenerate the electrode.

In some of any of the embodiments described herein, a method as described herein is effected in an oxygen-containing environment, as described herein.

Sample:

A peroxide-containing compound is used herein to describe organic and inorganic compounds that include one or more peroxides [—O—O—]. The compound can be comprised of an aliphatic or alicyclic or aromatic hydrocarbon moiety, substituted by one or more peroxide-containing groups such as, for example, O—OR groups, with R being alkyl, cycloalkyl, aryl, hydrogen and the like. The hydrocarbon moiety can optionally be interrupted by one or more heteroatoms, such as nitrogen, oxygen, sulfur, phosphor, silicon, boron. The hydrocarbon moiety can optionally be further substituted by other substituents, as described herein. Alternatively, or in addition, the compound can be comprised of a hydrocarbon (e.g., aliphatic or alicyclic) interrupted by one or peroxide groups.

Peroxide-containing explosives are typically cyclic compounds, which include one or more peroxides interrupting the cyclic hydrocarbon, and may optionally be substituted and/or include additional interrupting heteroatoms. Examples include, but are not limited to, TATP, HMDT and TMDD.

Linear peroxide-containing explosives are also contemplated, as well as inorganic peroxide-containing compounds or compounds capable of generating peroxide-containing compounds.

Herein, the term "peroxide-containing compound" or "peroxide-containing material" does not encompass hydrogen peroxide.

For any one of the embodiments described herein, the sample encompasses samples suspected as containing a peroxide-containing compound, such that the systems and methods described herein are utilized for determining a presence and optionally an amount of a peroxide-containing compound and further optionally an identity (e.g., the chemical composition) of a peroxide-containing compound. Optionally, the sample is known to contain a peroxide-containing compound and the methods and systems described herein are utilized for determining an amount and/or identity of the peroxide-containing compound in the sample.

For any of the embodiments described herein, the methods and systems described herein can be used for identifying a presence or absence of a peroxide-containing compound as described herein, and can be efficiently utilized for discriminating a peroxide-containing compound (e.g., peroxide-containing explosives) from chemically-related compounds or mixtures of compounds (e.g., hydrogen peroxide).

For example, when a sample is suspected as containing a peroxide-containing compound which is an explosive, the methods and systems described herein can be used to determine if the compound is a peroxide-containing compound or a chemically-related non-explosive compound such as hydrogen peroxide.

As used herein, the term "explosive" encompasses an explosive material, an explosive residue (e.g., a substance obtained upon explosion) and a material associated with an explosive material (e.g., a starting material for preparing an explosive material).

Herein, a peroxide-containing compound is also referred to interchangeably as an analyte.

In some of any of the embodiments described herein, the sample is a fluid sample, and can be a liquid sample or a gaseous sample.

In some of any of the embodiments described herein, the sample is air.

In some of any of the embodiments described herein, the peroxide-containing compound is in a fluid state (e.g., is in a liquid state or a gaseous state).

The term "fluid" is defined as a substance that tends to flow and to conform to the outline of its container. Typical fluids include liquids and gasses, but may also include free flowing solid particles.

In some of any of the embodiments described herein, the peroxide-containing compound is in a gaseous state.

By "gaseous state" it is meant that at least a portion of the compound is in a form of vapors. Thus, for example, the compound can be a liquid or a solid at room temperature, yet, it is volatile to some extent, such that a portion thereof is in a gaseous state at room temperature. Alternatively, the compound can be in such a gaseous state upon heating a sample containing same.

Since, as noted herein, the method and system described herein can be utilized for detecting ultra-trace amounts of peroxide-containing compounds, the portion of a compound in a gaseous state can be ultra-law, as is further detailed hereinbelow.

In some of any of the embodiments described herein, a concentration of the peroxide-containing compound in the sample is lower than 1 micromolar.

The concentration of the peroxide-containing compound encompasses a concentration of the compound's vapors in air or other gaseous samples, as well as a concentration of the compound in a liquid sample.

Accordingly, in some of any of the embodiments described herein, the method and system described herein can be utilized to detect low-volatile peroxide-containing compounds, without concentrating the sample and/or heating the sample prior to contacting it with the system.

Since, as noted herein, the method and system described herein can be utilized for detecting ultra-trace amounts of peroxide-containing compounds, the portion of a compound in a gaseous state can be ultra-law, as is further detailed hereinbelow.

In some of any of the embodiments described herein, a concentration of the peroxide-containing compound in the sample is lower than 1 micromolar.

The concentration of the peroxide-containing compound encompasses a concentration of the compound's vapors in air or other gaseous samples, as well as a concentration of the compound in a liquid sample.

Accordingly, in some of any of the embodiments described herein, the method and system described herein can be utilized to detect low-volatile peroxide-containing compounds, with ultra-low vapor pressure, without concentrating the sample and/or heating the sample prior to contacting it with the system.

In some of any of the embodiments described herein, the sample comprises two or more peroxide-containing compounds.

In some of any of the embodiments described herein, a sample comprises one or more peroxide-containing compounds, and one or more additional compounds of interest (target compounds or analytes).

In some of any of the embodiments described herein, the sample comprises oxygen.

If the sample is a gaseous sample (e.g. air), the sample inherently comprises oxygen, and when it is dissolved in an electrolyte, dissolved oxygen is also present in the electrolyte.

If the sample is a liquid sample, for example sea water or from any other water source, it also comprises dissolved oxygen.

A sample as described herein can be analyzed using the methods and systems as described herein per se, without further processing.

It is expected that during the life of a patent maturing from this application many relevant electrodes and electrochemical cell configurations will be developed and the scope of the term electrode and electrochemical cell is intended to include all such new technologies a priori.

As used herein the term "about" refers to ±10% or ±5%.

The terms "comprises", "comprising", "includes", "including", "having" and their conjugates mean "including but not limited to".

The term "consisting of" means "including and limited to".

The term "consisting essentially of" means that the composition, method or structure may include additional ingredients, steps and/or parts, but only if the additional ingredients, steps and/or parts do not materially alter the basic and novel characteristics of the claimed composition, method or structure.

As used herein, the singular form "a", "an" and "the" include plural references unless the context clearly dictates otherwise. For example, the term "a compound" or "at least one compound" may include a plurality of compounds, including mixtures thereof.

Throughout this application, various embodiments of this invention may be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

Whenever a numerical range is indicated herein, it is meant to include any cited numeral (fractional or integral) within the indicated range. The phrases "ranging/ranges between" a first indicate number and a second indicate number and "ranging/ranges from" a first indicate number "to" a second indicate number are used herein interchangeably and are meant to include the first and second indicated numbers and all the fractional and integral numerals therebetween.

As used herein the term "method" refers to manners, means, techniques and procedures for accomplishing a given task including, but not limited to, those manners, means, techniques and procedures either known to, or readily developed from known manners, means, techniques and procedures by practitioners of the chemical, pharmacological, biological, biochemical and medical arts.

As used herein, the term "amine" describes both a —NR'R" group and a —NR'— group, wherein R' and R" are each independently hydrogen, alkyl, cycloalkyl, aryl, as these terms are defined hereinbelow.

The amine group can therefore be a primary amine, where both R' and R" are hydrogen, a secondary amine, where R' is hydrogen and R" is alkyl, cycloalkyl or aryl, or a tertiary amine, where each of R' and R" is independently alkyl, cycloalkyl or aryl.

Alternatively, R' and R" can each independently be hydroxyalkyl, trihaloalkyl, cycloalkyl, alkenyl, alkynyl, aryl, heteroaryl, heteroalicyclic, amine, halide, sulfonate, sulfoxide, phosphonate, hydroxy, alkoxy, aryloxy, thiohydroxy, thioalkoxy, thioaryloxy, cyano, nitro, azo, sulfonamide, carbonyl, C-carboxylate, O-carboxylate, N-thiocarbamate, O-thiocarbamate, urea, thiourea, N-carbamate, O-carbamate, C-amide, N-amide, guanyl, guanidine and hydrazine.

The term "amine" is used herein to describe a —NR'R" group in cases where the amine is an end group, as defined hereinunder, and is used herein to describe a —NR'— group in cases where the amine is a linking group.

Herein throughout, the phrase "end group" describes a group (a substituent) that is attached to another moiety in the compound via one atom thereof.

The phrase "linking group" describes a group (a substituent) that is attached to another moiety in the compound via two or more atoms thereof.

The term "alkyl" describes a saturated aliphatic hydrocarbon including straight chain and branched chain groups. Preferably, the alkyl group has 1 to 20 carbon atoms. Whenever a numerical range; e.g., "1-20", is stated herein, it implies that the group, in this case the alkyl group, may contain 1 carbon atom, 2 carbon atoms, 3 carbon atoms, etc., up to and including 20 carbon atoms. More preferably, the alkyl is a medium size alkyl having 1 to 10 carbon atoms. Most preferably, unless otherwise indicated, the alkyl is a lower alkyl having 1 to 5 carbon atoms. The alkyl group may be substituted or unsubstituted. Substituted alkyl may have one or more substituents, whereby each substituent group can independently be, for example, hydroxyalkyl, trihaloalkyl, cycloalkyl, alkenyl, alkynyl, aryl, heteroaryl, heteroalicyclic, amine, halide, sulfonate, sulfoxide, phosphonate, hydroxy, alkoxy, aryloxy, thiohydroxy, thioalkoxy, thioaryloxy, cyano, nitro, azo, sulfonamide, C-carboxylate, O-carboxylate, N-thiocarbamate, O-thiocarbamate, urea, thiourea, N-carbamate, O-carbamate, C-amide, N-amide, guanyl, guanidine and hydrazine.

The alkyl group can be an end group, as this phrase is defined hereinabove, wherein it is attached to a single adjacent atom, or a linking group, as this phrase is defined hereinabove, which connects two or more moieties via at least two carbons in its chain.

The term "aminoalkyl" is used herein to describe an alkyl substituted by an amine, as defined herein. In some embodiments, the amine substitutes a terminal carbon atom in the alkyl.

The term "cycloalkyl" describes an all-carbon monocyclic or fused ring (i.e., rings which share an adjacent pair of carbon atoms) group where one or more of the rings does not have a completely conjugated pi-electron system. The cycloalkyl group may be substituted or unsubstituted. Substituted cycloalkyl may have one or more substituents, whereby each substituent group can independently be, for example, hydroxyalkyl, trihaloalkyl, cycloalkyl, alkenyl, alkynyl, aryl, heteroaryl, heteroalicyclic, amine, halide, sulfonate, sulfoxide, phosphonate, hydroxy, alkoxy, aryloxy, thiohydroxy, thioalkoxy, thioaryloxy, cyano, nitro, azo, sulfonamide, C-carboxylate, O-carboxylate, N-thiocarbamate, O-thiocarbamate, urea, thiourea, N-carbamate, O-carbamate, C-amide, N-amide, guanyl, guanidine and hydrazine. The cycloalkyl group can be an end group, as this phrase is defined hereinabove, wherein it is attached to a single adjacent atom, or a linking group, as this phrase is defined hereinabove, connecting two or more moieties at two or more positions thereof.

The term "aryl" describes an all-carbon monocyclic or fused-ring polycyclic (i.e., rings which share adjacent pairs of carbon atoms) groups having a completely conjugated pi-electron system. The aryl group may be substituted or unsubstituted. Substituted aryl may have one or more substituents, whereby each substituent group can independently be, for example, hydroxyalkyl, trihaloalkyl, cycloalkyl, alkenyl, alkynyl, aryl, heteroaryl, heteroalicyclic, amine, halide, sulfonate, sulfoxide, phosphonate, hydroxy, alkoxy, aryloxy, thiohydroxy, thioalkoxy, thioaryloxy, cyano, nitro, azo, sulfonamide, C-carboxylate, O-carboxylate, N-thiocarbamate, O-thiocarbamate, urea, thiourea, N-carbamate, O-carbamate, C-amide, N-amide, guanyl, guanidine and hydrazine. The aryl group can be an end group, as this term is defined hereinabove, wherein it is attached to a single adjacent atom, or a linking group, as this term is defined hereinabove, connecting two or more moieties at two or more positions thereof.

The term "heteroaryl" describes a monocyclic or fused ring (i.e., rings which share an adjacent pair of atoms) group having in the ring(s) one or more atoms, such as, for example, nitrogen, oxygen and sulfur and, in addition, having a completely conjugated pi-electron system. Examples, without limitation, of heteroaryl groups include pyrrole, furane, thiophene, imidazole, oxazole, thiazole, pyrazole, pyridine, pyrimidine, quinoline, isoquinoline and purine. The heteroaryl group may be substituted or unsubstituted. Substituted heteroaryl may have one or more substituents, whereby each substituent group can independently be, for example, hydroxyalkyl, trihaloalkyl, cycloalkyl, alkenyl, alkynyl, aryl, heteroaryl, heteroalicyclic, amine, halide, sulfonate, sulfoxide, phosphonate, hydroxy, alkoxy, aryloxy, thiohydroxy, thioalkoxy, thioaryloxy, cyano, nitro, azo, sulfonamide, C-carboxylate, O-carboxylate, N-thiocarbamate, O-thiocarbamate, urea, thiourea, O-carbamate, N-carbamate, C-amide, N-amide, guanyl, guanidine and hydrazine. The heteroaryl group can be an end group, as this phrase is defined hereinabove, where it is attached to a single adjacent atom, or a linking group, as this phrase is defined hereinabove, connecting two or more moieties at two or more positions thereof. Representative examples are pyridine, pyrrole, oxazole, indole, purine and the like.

The term "heteroalicyclic" describes a monocyclic or fused ring group having in the ring(s) one or more atoms such as nitrogen, oxygen and sulfur. The rings may also have one or more double bonds. However, the rings do not have a completely conjugated pi-electron system. The heteroalicyclic may be substituted or unsubstituted. Substituted heteroalicyclic may have one or more substituents, whereby each substituent group can independently be, for example, hydroxyalkyl, trihaloalkyl, cycloalkyl, alkenyl, alkynyl, aryl, heteroaryl, heteroalicyclic, amine, halide, sulfonate, sulfoxide, phosphonate, hydroxy, alkoxy, aryloxy, thiohydroxy, thioalkoxy, thioaryloxy, cyano, nitro, azo, sulfonamide, C-carboxylate, O-carboxylate, N-thiocarbamate, O-thiocarbamate, urea, thiourea, O-carbamate, N-carbamate, C-amide, N-amide, guanyl, guanidine and hydrazine. The heteroalicyclic group can be an end group, as this phrase is defined hereinabove, where it is attached to a single adjacent atom, or a linking group, as this phrase is defined hereinabove, connecting two or more moieties at two or more positions thereof. Representative examples are piperidine, piperazine, tetrahydrofurane, tetrahydropyrane, morpholino and the like.

The term "amine-oxide" describes a —N(OR')(R") or a —N(OR')— group, where R' and R" are as defined herein. This term refers to a —N(OR')(R") group in cases where the amine-oxide is an end group, as this phrase is defined hereinabove, and to a —N(OR')— group in cases where the amine-oxime is an end group, as this phrase is defined hereinabove.

The term "halide" and "halo" describes fluorine, chlorine, bromine or iodine.

The term "haloalkyl" describes an alkyl group as defined above, further substituted by one or more halide.

The term "sulfate" describes a —O—S(=O)$_2$—OR' end group, as this term is defined hereinabove, or an —O—S(=O)$_2$—O— linking group, as these phrases are defined hereinabove, where R' is as defined hereinabove.

The term "thiosulfate" describes a —O—S(=S)(=O)—OR' end group or a —O—S(=S)(=O)—O— linking group, as these phrases are defined hereinabove, where R' is as defined hereinabove.

The term "sulfite" describes an —O—S(=O)—O—R' end group or a —O—S(=O)—O— group linking group, as these phrases are defined hereinabove, where R' is as defined hereinabove.

The term "thiosulfite" describes a —O—S(=S)—O—R' end group or an —O—S(=S)—O— group linking group, as these phrases are defined hereinabove, where R' is as defined hereinabove.

The term "sulfinate" describes a —S(=O)—OR' end group or an —S(=O)—O— group linking group, as these phrases are defined hereinabove, where R' is as defined hereinabove.

The term "sulfoxide" or "sulfinyl" describes a —S(=O)R' end group or an —S(=O)— linking group, as these phrases are defined hereinabove, where R' is as defined hereinabove.

The term "sulfonate" describes a —S(=O)$_2$—R' end group or an —S(=O)$_2$— linking group, as these phrases are defined hereinabove, where R' is as defined herein. The term "S-sulfonamide" describes a —S(=O)₂—NR'R" end group or a —S(=O)₂—NR'— linking group, as these phrases are defined hereinabove, with R' and R" as defined herein.

The term "N-sulfonamide" describes an R'S(=O)₂—NR"— end group or a —S(=O)₂—NR'— linking group, as these phrases are defined hereinabove, where R' and R" are as defined herein.

The term "disulfide" refers to a —S—SR' end group or a —S—S— linking group, as these phrases are defined hereinabove, where R' is as defined herein.

The term "carbonyl" or "carbonate" as used herein, describes a —C(=O)—R' end group or a —C(=O)— linking group, as these phrases are defined hereinabove, with R' as defined herein.

The term "thiocarbonyl" as used herein, describes a —C(=S)—R' end group or a —C(=S)— linking group, as these phrases are defined hereinabove, with R' as defined herein.

The term "oxime" describes a =N—OH end group or a =N—O— linking group, as these phrases are defined hereinabove.

The term "hydroxyl" describes a —OH group.

The term "alkoxy" describes both an —O-alkyl and an —O-cycloalkyl group, as defined herein.

The term "aryloxy" describes both an —O-aryl and an —O-heteroaryl group, as defined herein.

The term "thiohydroxy" describes a —SH group.

The term "thioalkoxy" describes both a —S-alkyl group, and a —S-cycloalkyl group, as defined herein.

The term "thioaryloxy" describes both a —S-aryl and a —S-heteroaryl group, as defined herein.

The term "cyano" describes a —C≡N group.

The term "isocyanate" describes an —N=C=O group.

The term "nitro" describes an —NO₂ group.

The term "acyl halide" describes a —(C=O)R"" group wherein R"" is halide, as defined hereinabove.

The term "azo" or "diazo" describes an —N=NR' end group or an —N=N— linking group, as these phrases are defined hereinabove, with R' as defined hereinabove.

The term "C-carboxylate" describes a —C(=O)—OR' end group or a —C(=O)—O— linking group, as these phrases are defined hereinabove, where R' is as defined herein.

The term "O-carboxylate" describes a —OC(=O)R' end group or a —OC(=O)— linking group, as these phrases are defined hereinabove, where R' is as defined herein.

The term "C-thiocarboxylate" describes a —C(=S)—OR' end group or a —C(=S)—O— linking group, as these phrases are defined hereinabove, where R' is as defined herein.

The term "O-thiocarboxylate" describes a —OC(=S)R' end group or a —OC(=S)— linking group, as these phrases are defined hereinabove, where R' is as defined herein.

The term "N-carbamate" describes an R"OC(=O)—NR'— end group or a —OC(=O)—NR'— linking group, as these phrases are defined hereinabove, with R' and R" as defined herein.

The term "O-carbamate" describes an —OC(=O)—NR'R" end group or an —OC(=O)—NR'— linking group, as these phrases are defined hereinabove, with R' and R" as defined herein.

The term "O-thiocarbamate" describes a —OC(=S)—NR'R" end group or a —OC(=S)—NR'— linking group, as these phrases are defined hereinabove, with R' and R" as defined herein.

The term "N-thiocarbamate" describes an R"OC(=S)NR'— end group or a —OC(=S)NR'— linking group, as these phrases are defined hereinabove, with R' and R" as defined herein.

The term "S-dithiocarbamate" describes a —SC(=S)—NR'R" end group or a —SC(=S)NR'— linking group, as these phrases are defined hereinabove, with R' and R" as defined herein.

The term "N-dithiocarbamate" describes an R"SC(=S)NR'— end group or a —SC(=S)NR'— linking group, as these phrases are defined hereinabove, with R' and R" as defined herein.

The term "urea", which is also referred to herein as "ureido", describes a —NR'C(=O)—NR"R''' end group or a —NR'C(=O)—NR"— linking group, as these phrases are defined hereinabove, where R' and R" are as defined herein and R''' is as defined herein for R' and R".

The term "thiourea", which is also referred to herein as "thioureido", describes a —NR'—C(=S)—NR"R''' end group or a —NR'—C(=S)—NR"— linking group, with R', R" and R''' as defined herein.

The term "C-amide" describes a —C(=O)—NR'R" end group or a —C(=O)—NR'— linking group, as these phrases are defined hereinabove, where R' and R" are as defined herein.

The term "N-amide" describes a R'C(=O)—NR"— end group or a R'C(=O)—N—linking group, as these phrases are defined hereinabove, where R' and R" are as defined herein.

The term "guanyl" describes a R'R"NC(=N)— end group or a —R'NC(=N)— linking group, as these phrases are defined hereinabove, where R' and R" are as defined herein.

The term "guanidine" describes a —R'NC(=N)—NR"R''' end group or a —R'NC(=N)—NR"— linking group, as these phrases are defined hereinabove, where R', R" and R''' are as defined herein.

The term "hydrazine" describes a —NR'—NR"R''' end group or a —NR'—NR"— linking group, as these phrases are defined hereinabove, with R', R", and R''' as defined herein.

The term "silyl" describes a —SiR'R"R''' end group or a —SiR'R"— linking group, as these phrases are defined hereinabove, whereby each of R', R" and R''' are as defined herein.

The term "siloxy" describes a —Si(OR')R"R''' end group or a —Si(OR')R"— linking group, as these phrases are defined hereinabove, whereby each of R', R" and R''' are as defined herein.

The term "silaza" describes a —Si(NR'R")R''' end group or a —Si(NR'R")— linking group, as these phrases are defined hereinabove, whereby each of R', R" and R''' is as defined herein.

The term "silicate" describes a —O—Si(OR')(OR") (OR''') end group or a —O—Si(OR')(OR")— linking group, as these phrases are defined hereinabove, with R', R" and R''' as defined herein.

As used herein, the term "hydrazide" describes a —C(=O)—NR'—NR"R''' end group or a —C(=O)—NR'—NR"— linking group, as these phrases are defined hereinabove, where R', R" and R''' are as defined herein.

As used herein, the term "thiohydrazide" describes a —C(=S)—NR'—NR"R''' end group or a —C(=S)—NR'—NR"— linking group, as these phrases are defined hereinabove, where R', R" and R''' are as defined herein.

As used herein, the term "methyleneamine" describes an —NR'—CH₂—CH=CR"R''' end group or a —NR'—

CH$_2$—CH=CR'''— linking group, as these phrases are defined hereinabove, where R', R" and R''' are as defined herein.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination or as suitable in any other described embodiment of the invention. Certain features described in the context of various embodiments are not to be considered essential features of those embodiments, unless the embodiment is inoperative without those elements.

Various embodiments and aspects of the present invention as delineated hereinabove and as claimed in the claims section below find experimental support in the following examples.

EXAMPLES

Reference is now made to the following examples, which together with the above descriptions illustrate some embodiments of the invention in a non limiting fashion.

Materials and Methods

Spectracarb™ 2050A-1050 carbon paper microelectrode, 0.18 mm thick was obtained from Engineered Fiber Technology, USA. Electrode samples having an area of 0.35 cm$^2$ were used in all experiments, unless otherwise indicated.

Nickel foil (thickness of 0.125 mm, ≥99.9%), Tetrabutylammonium iodide (TBA-I≥98.0%, electrochemical grade), Acetonitrile (99.8%), and Ethanol (≥99.5%), were purchased from Sigma-Aldrich, Israel.

Silver benzoate (99%) was obtained from Sigma-Aldrich, Israel

Nafion® 117 solution was obtained from Sigma-Aldrich, Israel.

Hexamethylenetetramine (99+ %), tetra-n-butylammoniumtetrafluoroborate (TBABF$_4$, 99+ %, electrochemical grade), hydrogen peroxide (30%), anhydrous citric acid (99.5+ %), sulfuric acid (95-98%), silver benzoate (99%), acetone (99.8+ %), acetonitrile (99.8%), N, N-dimethylformamide (99.8%), ethanol (99.5+ %), and 1, 2-dichloroethane (99.8%) were purchased from Sigma-Aldrich, Israel.

Triacetonetriperoxide (TATP) was synthesized by a reaction of acetone with 30% H$_2$O$_2$ in the presence of sulfuric acid at −20° C., as described in Oxley et al. *Propell Explos Pyrot* 27, 209-216, 2002.

Hexamethylenetriperoxide diamine (HMTD) was obtained by the reaction of hexamethylenetetramine with 30% H$_2$O$_2$ in the presence of anhydrous citric acid at 0° C.

Parafilm PM996 was purchased from Alex Red, Israel.

All other reagents were obtained from known vendors.

Millipore Mill-Q water (deionized water, 18 mega-ohm) was used in all experiments.

Scanning electron microscope (SEM) measurements were performed using Quanta 200 FEG environmental scanning electron microscope.

X-ray Photoelectron Spectroscopy (XPS) measurements were performed in UHV (2.5×10$^{-10}$ Torr base pressure) using 5600 Multi-Technique System (PHI, USA). The sample was irradiated with an Al K$_\alpha$ monochromated source (1486.6 eV) and the outcome electrons were analyzed by a Spherical Capacitor Analyzer using the slit aperture of 0.8 mm. The samples were analyzed at the surface only. They were uncharged during measurements.

A three-electrode electrochemical cell (volume 3 ml) was used in all experiments, unless otherwise indicated, in which a glassy carbon electrode was used as the counter electrode, a silver-silver chloride (Ag—AgCl), with 3 molar potassium chloride, was used as the reference electrode with a double junction salt bridge (Metrohm), and micro-carbon-fibers (0.35 cm$^2$, 0.18 mm in diameter), or micro-carbon-fibers chemical modified electrode (0.35 cm$^2$, 0.18 mm in diameter) was used as the working electrode.

A non-modified working electrode was prepared from micro-carbon-fibers paper (0.18×20×5 mm), and nickel foil (0.2×25×5 mm) as a current collector (electrical contact); the connection and the insulation of micro-carbon-fibers with nickel contact was performed by Parafilm. The electrode with current collector was pressed with a pressure of about 2 kg/cm$^2$ for 30 seconds at room temperature. The electrode was carefully washed with ethanol, rinsed with distilled water and dried at room temperature.

Linear sweep and cyclic voltammetries were performed using Autolab PGSTAT 302N. The scan rate of performed linear sweep voltammetry registration was 0.1 volt/second.

Example 1

TATP and H$_2$O$_2$ Reduction Peaks Obtained by Unmodified CF Microelectrode

As background reference experiments, the electrochemical detection of peroxide-based explosives in the presence of H$_2$O$_2$ and dissolved oxygen was performed using unmodified carbon fiber (CF) microelectrode having a surface area of 0.35 cm$^2$. A high-pH electrolyte solution was selected, assuming it may influence the stability of the H$_2$O$_2$ and decrease the reduction potential of H$_2$O$_2$ compared to peroxide based explosives. The selected solution contained a mixture of NaOH in deionized water (pH=12) and acetonitrile at 7:3 volume ratio and 0.1 M TBABF$_4$.

Linear sweep voltammetry registration was performed at a scan rate of 0.1 volt/second.

The obtained data is presented in FIG. 1. The black line represents the background without TATP addition, the red, blue and turquoise lines represent the background with 20, 40 and 60 ppm of TATP addition respectively, and the pink line represents the background with 60 ppm TATP and 40 ppm H$_2$O$_2$.

As shown in FIG. 1, the high pH conditions did not result in separation of the two reduction peaks, and the reduction potentials of both H$_2$O$_2$ and TATP on the unmodified electrode were both around 1.35 volt.

Example 2

HMTD and H$_2$O$_2$ Reduction Peaks Obtained by Silver Benzoate-Modified CF Microelectrode The present inventors have conceived utilizing the catalytic activity of silver in H$_2$O$_2$ decomposition reaction for promoting the separation of H$_2$O$_2$ and peroxide-based explosives current peaks. To this effect, the present inventors have sought for a stable silver modification of the CF microelectrode, and have used silver benzoate and Nafion® modification.

A modification of a CF microelectrode with silver benzoate was carried out by tipping 15 μl of 1% silver benzoate and 1% Nafion® 117 in ethanol on the electrode and air-drying or N$_2$-drying at 40° C. for 60 minutes. Due to the organometallic properties of silver benzoate, the silver efficiently absorbed to the carbon microfibers.

The Nafion® serves as coating exchange membrane that prevents the washing of silver benzoate from the working electrode surface.

Linear sweep voltammetry registration was performed at a scan rate of 0.1 volt/second, while using a high pH electrolyte solution as described in Example 1 herein.

The obtained data is presented in FIGS. 2A-C.

In FIG. 2A, the black line represents the background without HMDT addition, and the other lines represent the background with addition of HMDT at the indicated concentrations.

As shown in FIG. 2A, efficient separation of the H$_2$O$_2$ current peak, appearing at −0.4 Volts) from that of HMTD, appearing between −0.8 to −0.9 Volts, was obtained. A drift of the HMTD's current peak towards the negative spectrum of voltages in a concentration dependant manner was observed, indicating some instability of the modification.

FIG. 2B presents a calibration curve based on current peaks of HMTD as marked by a green arrow. ΔI=background current−current peak of HMTD. It can be seen that the detection of HMTD was performed in high concentration dependence (R=0.993).

FIG. 2C presents the data obtained upon addition of 180 ppm HMTD (black line) of 180 ppm HMTD and 40 ppm H$_2$O$_2$ (red line).

Example 3

Scanning Electron Microscope and X-Ray Photoelectron Spectroscopy Analyses of Silver Benzoate Modified CF Microelectrode The CF microelectrode surface was analyzed by scanning electron microscope (SEM) using secondary electrons (SE) and backscattered electrons (BSE). Then atomic concentrations of carbon (C), oxygen (O), silver (Ag), fluorine (F), sulfur (S), were determined using X-ray photoelectron spectroscopy atomic (XPS) concentrations. The surface analyses of the unmodified CF microelectrode are presented in FIG. 3A. The surface analyses of the silver benzoate-modified CF microelectrode after performing one linear sweep voltammetry scans from 0 volts to −1.6 volts, at a scan rate of 0.1 volt/second in the electrolyte solution as described in Example 1 herein are presented in FIG. 3B. The surface analyses of the modified CF microelectrode after performing 100 linear sweep voltammetry scans from 0 volts to −1.6 volts, at a scan rate of 0.1 volt/second in the electrolyte solution as described in Example 1 herein is presented in FIG. 3C.

The unmodified CF microelectrode was first analyzed using scanning electron microscope (SEM) by secondary electrons (SE) and backscattered electrons (BSE). The obtained data is presented in FIG. 3A (right panel), and show that the CF microelectrode is composed of rough fibers with few microns width, which contributed to the active surface area of the electrode.

After the modification with silver benzoate and use in one linear sweep voltammetry scan of from 0 volts to −1.6 volts, with addition of TATP to the electrolyte, the SEM-SE and SEM-BSE images, presented in FIG. 3B, right panel, show a formation of silver nano-particles distributed in low density around the carbon fibers surface.

After the modified micro-carbon-fibers electrode was used for 100 repetitions of the same electrochemical measurement, the SEM-SE and SEM-BSE, presented in FIG. 3B, right panel, showed an increased amount and distribution of the silver nano-particles around the carbon fibers surface.

These findings suggest that the voltage applied to the surface of the electrode leads to reduction of the silver benzoate and formation of silver nanoparticles, which changes the surface area and the chemical properties of the electrode.

The reduction of silver benzoate as a result of the electrochemical measurement is shown in the X-ray photoelectron spectroscopy (XPS) data obtained. The XPS analysis shows a decrease in the atomic concentration of organometallic (Organo Ag) and silver oxide (Oxide Ag) on the surface of the modified CF microelectrode after 100 repetitions of electrochemical measurements of linear sweep voltammetry scan from 0 volts to −1.6 volts (see, FIG. 3C, left panel). The atomic concentration of metallic silver (Metallic Ag) increased as a result of the performed 100 electrochemical measurements (see, FIG. 3C, left panel).

The presence of fluorine (F) and sulfur (S) indicated a successful modification by Nafion on the electrode surface. See, FIGS. 3B and 3C, left panels.

X-ray crystallography (RXD) analysis showed that the average size of the formed silver nano-particles as a result of the electrochemical measurement was about 40 nm (data not shown).

Example 4

Detection of TATP and HMTD in the Presence of Dissolved Oxygen and H$_2$O$_2$

In an attempt to stabilize the silver benzoate modification and obtain reproducible current peaks of peroxide-based explosives, the linear sweep voltammetry scans from 0 volts to −1.6 volts were performed in the electrolyte solution 10-15 subsequent times prior to the detection of peroxide based explosives.

The data obtained upon addition of HMTD, following 15 subsequent repetitions of the linear sweep voltammetry scans is presented in FIGS. 4A-C. The data obtained upon addition of TAPT, following 15 subsequent repetitions of the linear sweep voltammetry scans is presented in FIGS. 5A-C.

In FIGS. 4A and 5A, the black line represents data obtained for the background electrolyte without HMDT or TAPT addition, and the other lines represent the data obtained upon addition of HMDT or TAPT at the indicated concentrations.

As shown in FIGS. 4A and 5A, efficient separation of the H$_2$O$_2$ current peak, appearing at about −0.5 Volts, from that of HMTD, appearing at about −1.5 Volts, and of TAPT, appearing at about −1.4 Volts, was obtained. Importantly, no drift of the current peaks was observed. The H$_2$O$_2$ current peak barely affected the current peaks of HMTD and TATP.

The green arrow in FIGS. 4A and 5A represents the current peaks that were used for the calibration curve presented in FIGS. 4B and 5B, respectively. ΔI=background current−current peak of HMTD.

It can be seen that the detection of both peroxide-based explosives was performed in high concentration dependence (R=0.997), and could be distinguished by a characteristic shape of the peak FIG. 4C presents the data obtained upon addition of 150 ppm HMTD (black line) and of 150 ppm HMTD and 40 ppm H$_2$O$_2$ (red line).

FIG. 5C presents the data obtained upon addition of 180 ppm TATP (black line) and of 150 ppm TATP and 30 ppm $H_2O_2$ (red line).

The analysis of a single sample took 16 seconds, hence meets the need of field condition sensing of explosive.

These data indicate that utilization of stabilized silver nanoparticles micro-carbon-fibers electrode is an efficient method for the detection of peroxide-based explosives, in the presence of $H_2O_2$ and dissolved oxygen. The catalytic capabilities of this modification route enabled to perform current peak separation of peroxide-based explosives from $H_2O_2$ and $O_2$ peaks in a single measurement cycle of linear sweep voltammetry, without using time-consuming pre-processing steps. The whole measurement lasts approximately 10 seconds. The shape of the current peak and its voltage could be used to distinguish between different peroxide-based explosives, and thereby add multiplex capabilities to the detection method. A detection limit of the peroxide-based explosives using linear sweep voltammetry can be around 0.25 ppm. In order to further improve the detection limit a differential pulse voltammetry can be applied.

Thus, silver nanoparticles chemical modification of micro-carbon-fibers electrodes enabled to perform real-time, label-free, low cost, robust, selective and sensitive direct detection of peroxide-based explosives, such as TATP and HMTD, in sub-ppm level concentrations without applying pre-processing steps, thereby combining simplicity and rapid sampling rate.

Example 5

Gas Phase Detection of TATP

EmStat system was used for voltammetry registration in the linear sweep regimes. The scan rate of performed linear sweep voltammetry registration was 0.1 volt/second.

A conventional three-electrode cell (volume 3 ml), in which a glassy carbon electrode was used as the counter electrode, a silver-silver chloride (Ag—AgCl), with 3 molar potassium chloride, was used as the reference electrode with a double junction salt bridge (Metrohm), and a micro-carbon-fibers (0.35 cm$^2$, 0.18 mm thickness), or micro-carbon-fibers chemically modified electrode (0.35 cm$^2$, 0.18 mm thickness) was used as the working electrode. The background solution contained a mixture of sodium hydroxide in deionized water (pH=12), and acetonitrile at 7:3 volume ratio, 0.1 M tetra-n-butylammoniumtetrafluoroborate.

A modification of micro-carbon-fibers electrode with silver benzoate was carried out by dropping 15 μl of 1% silver benzoate and 1% Nafion® 117 in ethanol on the electrode surface and air-drying at 40° C. for 60 minutes.

TATP (prepared as described herein) was absorbed to a filter paper as a solution of 10 mg in ethanol. The soaked paper was placed in a closed box for about an hour prior to measurements to achieve TATP vapor saturation.

The vapors were then pumped by means of an air pump, through a tube that connected the TATP vapors, the tested electrode and the pump (in a configuration in which the vapors contact the electrode while being pumped).

The obtained data is presented in FIG. 7 and clearly show the detection of distinct signal.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention. To the extent that section headings are used, they should not be construed as necessarily limiting.

What is claimed is:

1. A sensing electrode comprising a carbon electrode and a functional moiety being in association with at least a portion of a surface of said electrode, said functional moiety comprising at least one metal species that promotes decomposition of hydrogen peroxide, wherein said functional moiety comprises an organic salt of said metal which comprises metal ions and organic anions and particles of said metal, wherein a mol ratio of said metal ions and said particles of said metal ranges from 70:30 to 30:70, and wherein said metal is silver.

2. The electrode of claim 1, wherein said electrode is a carbon fiber microelectrode.

3. The electrode of claim 1, wherein said carbon electrode is gas-permeable.

4. The electrode of claim 1, wherein said metal ion undergoes reduction to thereby provide metal particles, upon application of a potential in a range of from about −0.05 to about 2 volts.

5. The electrode of claim 1, wherein an amount of said particles of said metal is less than 70 mol %, or less than 65 mol %, of the total number of moles of said metal in said functional moiety.

6. The electrode of claim 1, wherein said organic salt of said metal is silver benzoate.

7. The electrode of claim 1, further comprising an ion-permeable material absorbed to said surface.

8. A sensing system comprising a sensing electrode according to claim 1, the sensing electrode being connectable to a power source.

9. The sensing system of claim 8, wherein said sensing electrode forms a part of an electrochemical cell.

10. The system of claim 9, wherein said electrochemical cell further comprises an electrolyte, and wherein at least a portion of said sensing electrode contacts said electrolyte.

11. The system of claim 10, wherein said electrolyte features an alkaline pH.

12. The system of claim 8, being devoid of means for deaerating the electrochemical cell prior to contacting the system with a sample.

13. The system of claim 8, further comprising a device for measuring an electrochemical parameter of said sensing electrode.

14. The system of claim 8, being configured such that upon application of a potential, a portion of said metal species is in a form of metal particles, said portion being no more than 70 mol % of the total amount of said metal species.

15. The system of claim 8, wherein said functional moiety comprises metal ions and wherein upon application of a potential, a portion of said metal ions is converted into said metal particles, said portion being no more than 50 mol % of the amount of said metal ions.

16. The system of claim 8, being configured such that upon contacting a sample containing a peroxide-containing compound with said sensing electrode, a presence and/or level of an electrochemical parameter generated in response to applying potential to said sensing electrode is indicative of a presence and/or level of the peroxide-containing compound.

17. A method of detecting a peroxide-containing compound in a sample, the method comprising:
   contacting the sample with a sensing electrode according to claim 1;
   applying a potential to the sensing electrode; and
   measuring an electrochemical parameter of said sensing electrode, wherein a presence and/or level of said parameter is indicative of a presence and/or level of the peroxide-containing compound in the sample.

18. The method of claim 17, wherein said electrochemical parameter comprises an electrical current generated at said sensing electrode, wherein a presence and/or level of said electrical current is indicative of a presence and/or level of the peroxide-containing compound.

19. The method of claim 17, wherein the sample comprises oxygen.

20. The method of claim 17, further comprising, prior to introducing said sample, repetitively applying said potential for at least 5 consecutive times.

21. The method of claim 20, wherein repetitively applying said potential is performed such that a portion of said metal species is converted to metal particles, said portion being no more than 50 mol % of the total amount of said metal species.

22. The method of claim 17, wherein said sensing electrode forms a part of a sensing system.

23. The method of claim 22, being devoid of deaerating the system.

* * * * *